(12) United States Patent
Nagai

(10) Patent No.: US 6,428,572 B2
(45) Date of Patent: *Aug. 6, 2002

(54) INTRAOCULAR RING

(75) Inventor: Hidenobu Nagai, Nagoya (JP)

(73) Assignee: Menicon Co., Ltd., Nagoya (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/227,971

(22) Filed: Jan. 11, 1999

(30) Foreign Application Priority Data

Jan. 12, 1998 (JP) .............................. 10-004202
Dec. 21, 1998 (JP) .............................. 10-362568

(51) Int. Cl.$^7$ ................................ A61F 2/16
(52) U.S. Cl. ................ 623/4.1; 623/5.12; 623/6.45; 623/906
(58) Field of Search ............... 623/5.12, 5.16, 623/5.11, 6.43, 906, 6.45, 6.46, 4.1; 606/107

(56) References Cited

U.S. PATENT DOCUMENTS

| | | | | |
|---|---|---|---|---|
| 4,666,444 A | * | 5/1987 | Pannu | 623/6 |
| 4,969,897 A | * | 11/1990 | Kalb | 623/6 |
| 5,323,788 A | * | 6/1994 | Silvestrini et al. | 623/5.12 |
| 5,522,887 A | * | 6/1996 | Hoe | 623/5.11 |
| 5,693,092 A | * | 12/1997 | Silestrini et al. | 623/5.12 |
| 5,824,086 A | * | 10/1998 | Silvestrini | 623/5.11 |
| 5,733,334 A | * | 1/1999 | Lee | 623/5 |
| 5,855,604 A | * | 1/1999 | Lee | 623/5 |

* cited by examiner

*Primary Examiner*—Paul B. Prebilic
(74) *Attorney, Agent, or Firm*—Armstrong, Westerman & Hattori, LLP

(57) ABSTRACT

It is an intraocular ring of open ring shape when inserting, so that it can be inserted from a small incision, and after being inserted into the capsule, by engaging the engaging mechanisms having mutually complementary male and female structures provided at ends of the intraocular ring, the intraocular ring having a nearly same compressive load as in closed ring is presented. Being made of an elastic material, it is an intraocular ring composed to contact with the entire inner circumference of the equatorial area in the capsule when inserted into the lenticular capsule, and engaging mechanisms are disposed at both ends in a partially cut-off state of the intraocular ring, and by engagement of the engaging mechanisms, a continuous ring shape without cut section is formed.

9 Claims, 37 Drawing Sheets

F I G. 23(a)
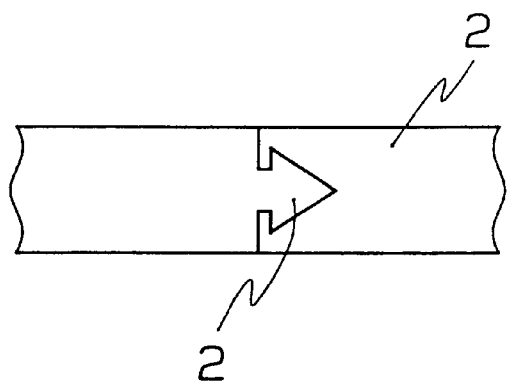
F I G. 23(b)
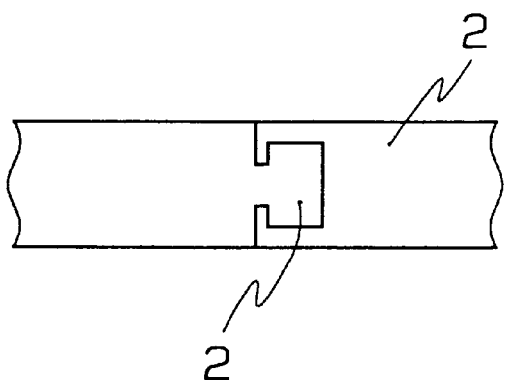
F I G. 23(c)
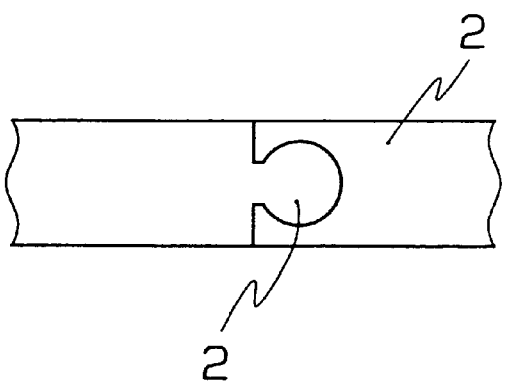
F I G. 23(d)
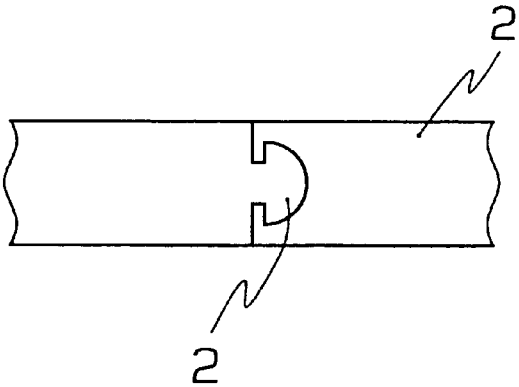

100

ND RING

BACKGROUND OF THE INVENTION

The present invention relates to an intraocular ring. More particularly, it relates to an intraocular ring to be worn inside of the equatorial area of a lenticular capsule (hereinafter called capsule) undergoing extracapsular cataract extraction (including phacoemulsification aspiration) for treatment of cataract in order to hold the capsule in a circular form.

Intraocular rings for retaining the shape of the capsule after extracapsular cataract extraction (including phacoemulsification aspiration) are roughly classified into the open ring as disclosed in Japanese Examined Patent Publication No. 51302/1993 (see FIG. 33 and FIG. 34), and the closed ring as disclosed in Japanese Examined Patent Publication No. 9582/1994 or Japanese Unexamined Patent Publication No. 364840/1992 (see FIG. 35, FIG. 36, and FIG. 37).

(1) It is an advantage of the open ring that the intraocular ring can be inserted easily into the capsule, but since the cut position of the ring is simultaneously movable, its demerit is that it is poor in the shape retaining property of the capsule following extracapsular cataract extraction (including phacoemulsification aspiration).

(2) In the case of a closed ring, after extracapsular cataract extraction (including phacoemulsification aspiration), as shown in FIG. 36 and FIG. 37, the capsule is filled up sufficiently with a viscous fluid, and an intraocular ring 100 is picked by forceps P (or injector (not shown) for soft lens) and deflected in a nearly rectangular shape, and the intraocular ring 100 is gradually inserted into the capsule through a cut S and a cut H. When inserted in the capsule, by the own elasticity of the intraocular ring 100, it restores the original annular shape and contacts with the whole circumference of the equatorial area of the capsule. Therefore, the closed ring is excellent in the shape retaining performance of the capsule after removal of the lens.

However, it requires a highly advanced skill in the operation of picking the intraocular ring 100 by the forceps P to deflect nearly in a rectangular form and inserting the intraocular ring 100 gradually into the capsule through the cut S and cut H, and it is difficult to insert the intraocular ring into the capsule. As compared with the open ring, yet, the cuts are larger, and troubles may be caused after operation (such as postoperative astigmatism).

On the other hand, European Patent Publication No. 0478929A1 discloses an intraocular ring (see FIG. 31 and FIG. 32) having a lock mechanism (locking achieved by inserting and engaging) 102 forming divided and plural step parts. In the case of this intraocular ring 100, after adjusting the diameter of the intraocular ring 100 by the lock mechanism 102, the intraocular ring 100 must be inserted into the capsule, and it cannot be inserted into the capsule in a divided state as in the above-mentioned open ring and the defects of the closed ring (2) are not solved.

Moreover, in the case of the intraocular ring disclosed in European Patent Publication No. 0478929A1, since the shrinking direction of the capsule and the ring size changing direction are identical, if a strong shrinkage occurs in the capsule, the ring size is also deformed. As a result, if part of the ring is adhered to the tissues, the original circular shape cannot be maintained but is deformed, which may lead to decentration of the intraocular lens.

It is hence an object of the invention to solve the problems of the prior arts, and present an intraocular ring, which is an open ring type intraocular ring when inserting, the intraocular ring capable of being inserted from small incision and, after being inserted into the capsule, is capable of obtaining a same compressive load as in the closed ring by engaging the engaging mechanisms having mutually complementary male and female structures provided at the ends of the intraocular ring.

SUMMARY OF THE INVENTION

The intraocular ring in one embodiment of the present invention is an intraocular ring made of an elastic material, defining a circular opening, and contacting with entire inner circumference of an equatorial area of a capsule after being inserted in the capsule, in which engaging mechanisms are provided at both ends, in a partially cut-off state of the intraocular ring, and a continuous ring shape without cut section is formed by engagement of the engaging mechanisms.

Preferably, the intraocular ring engaging mechanisms include mutually complementary male and female structures.

The intraocular ring in another embodiment of the present invention is a partially cut-off intraocular ring made of an elastic material, and contacting with entire inner circumference of an equatorial area of a capsule after being inserted in the capsule, in which a continuous shape is formed when the intraocular ring is inserted in the capsule as the both ends of the cut-off intraocular ring contact with each other.

Preferably, the both ends of the intraocular ring are formed in a taper.

The intraocular ring in still another embodiment of the present invention is an intraocular ring comprising two or three or more parts, made of an elastic material, and said intraocular ring contacting with entire inner circumference of an equatorial area of the capsule after being inserted in the capsule, in which the two or three or more parts individually have engaging mechanisms provided at both ends so that arbitrary adjacent parts may be engaged with each other in a male-female structure, and a continuous ring shape without cut section is formed when the two or three or more parts are mutually engaged with each other.

Preferably, a predetermined compressive load is applied in the engaged state of the cut sections of the ring, i.e., the ring is in elastic tension such that the ring would tend to reach the partially cut-off state, i.e. a discontinuous or open state.

Preferably, the compressive load is about 250 mgf or more.

Preferably, at least one end of both ends of the intraocular ring is provided with a flange, since circumferential or axial deviation of one end of the intraocular ring relative to the other end thereof is prevented.

An intraocular ring with an open ring shape for insertion is disclosed. It can be inserted from a small incision, and after inserting into the capsule, a compressive load nearly same as in the closed ring is obtained by engaging the engaging mechanisms having mutually complementary male and female structures provided at the ends of the intraocular ring.

Referring now to the accompanying drawings, the intraocular ring (hereinafter called the ring) of the invention is described in detail below.

BRIEF DESCRIPTION OF THE DRAWINGS

FIGS. 23(a) to 23(d) are partial side views each showing yet another example of an engaged state of the ring of FIGS. 16(a) to 16(d);

EMBODIMENT 1

Figure 1A:
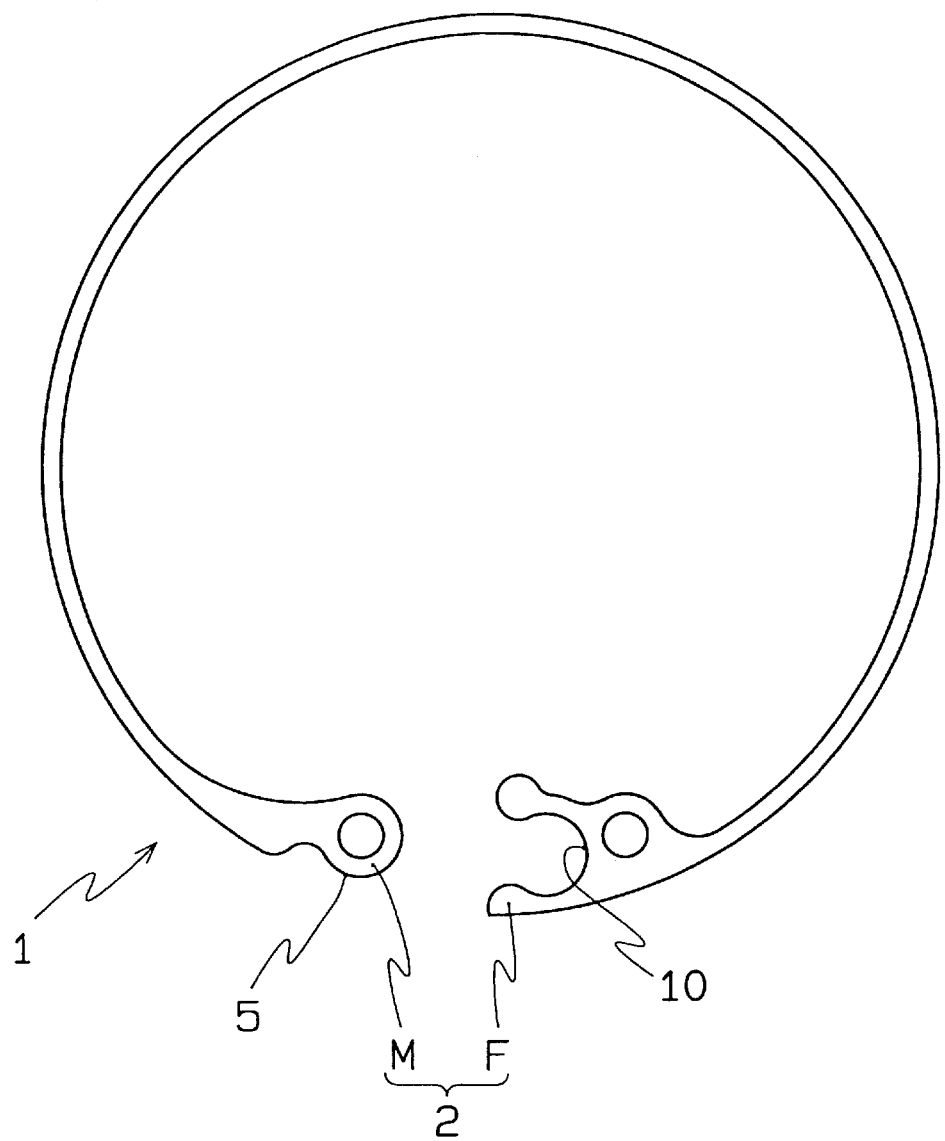
FIG. 1(a) is a plan view showing one example of an embodiment of ring of the present invention.
Figure 1B:
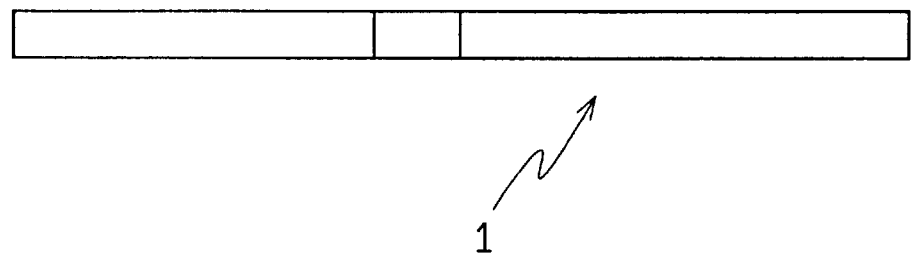
FIG. 1(b) is a sectional view showing an engaged state of the ring of FIG. 1(a)
Figure 2:
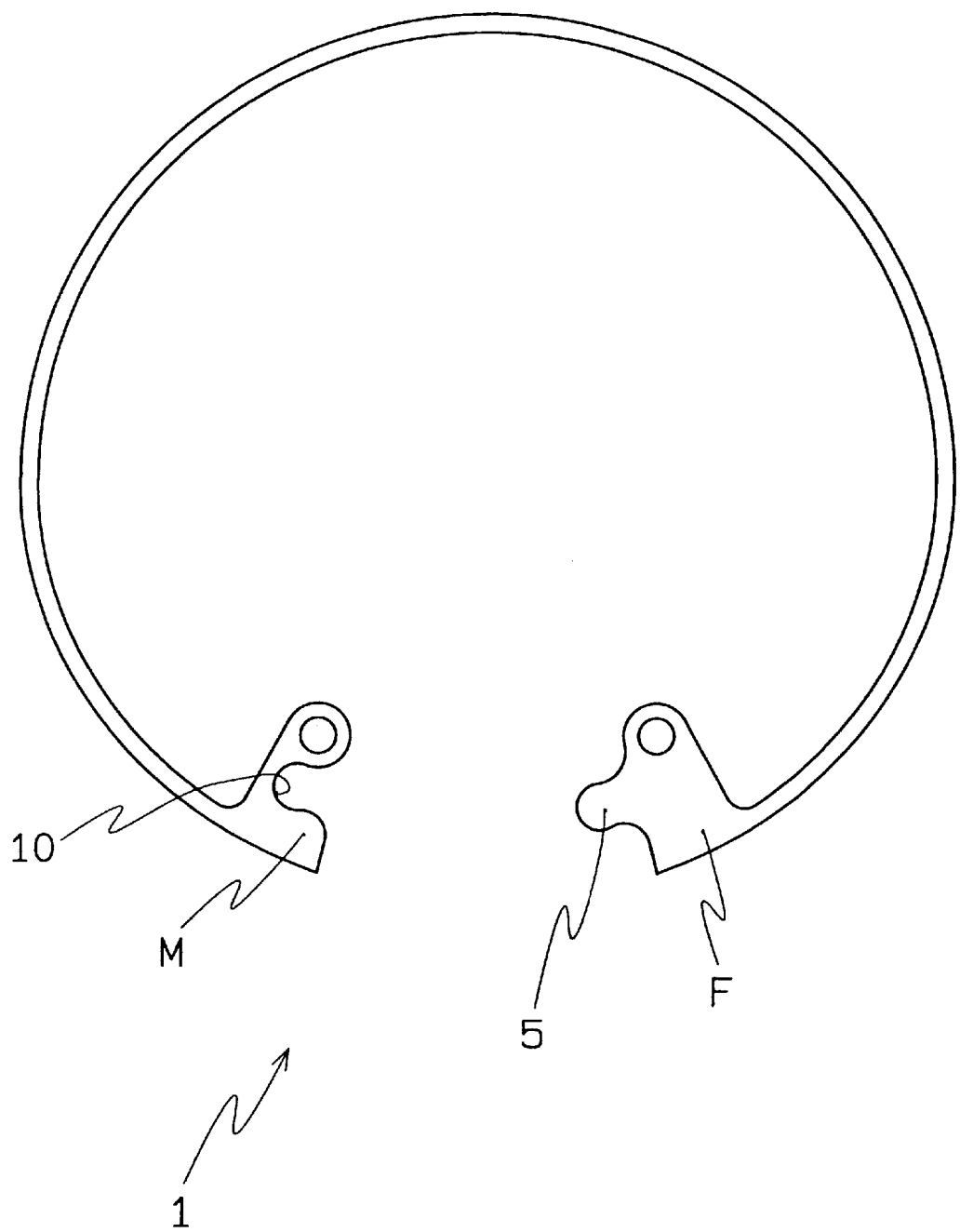
FIG. 2 is a plan view showing another example of the ring of FIGS. 1(a) and 1(b)
Figure 3:
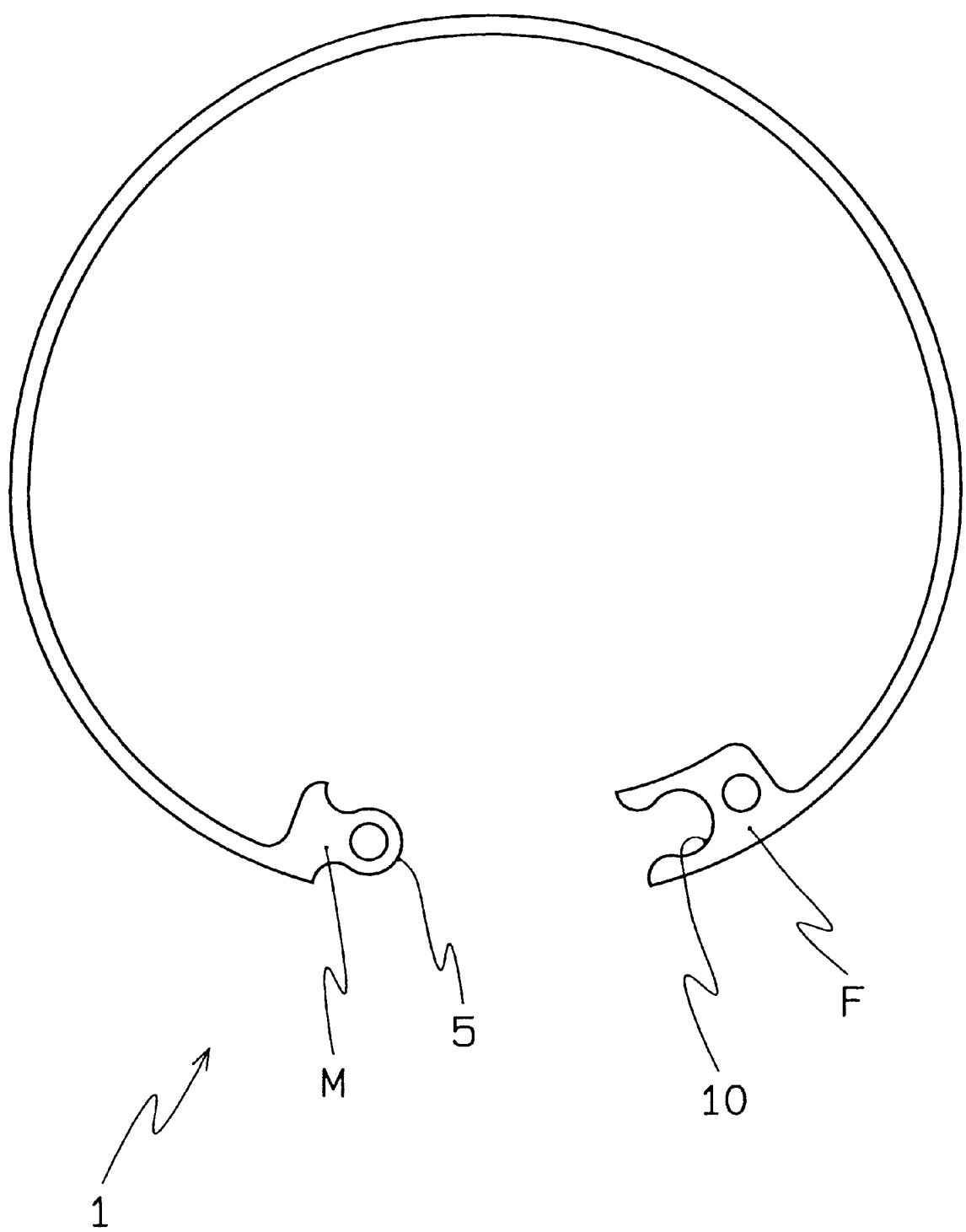
FIG. 3 is a plan view showing still another example of the ring of FIGS. 1(a) and 1(b)
Figure 4:
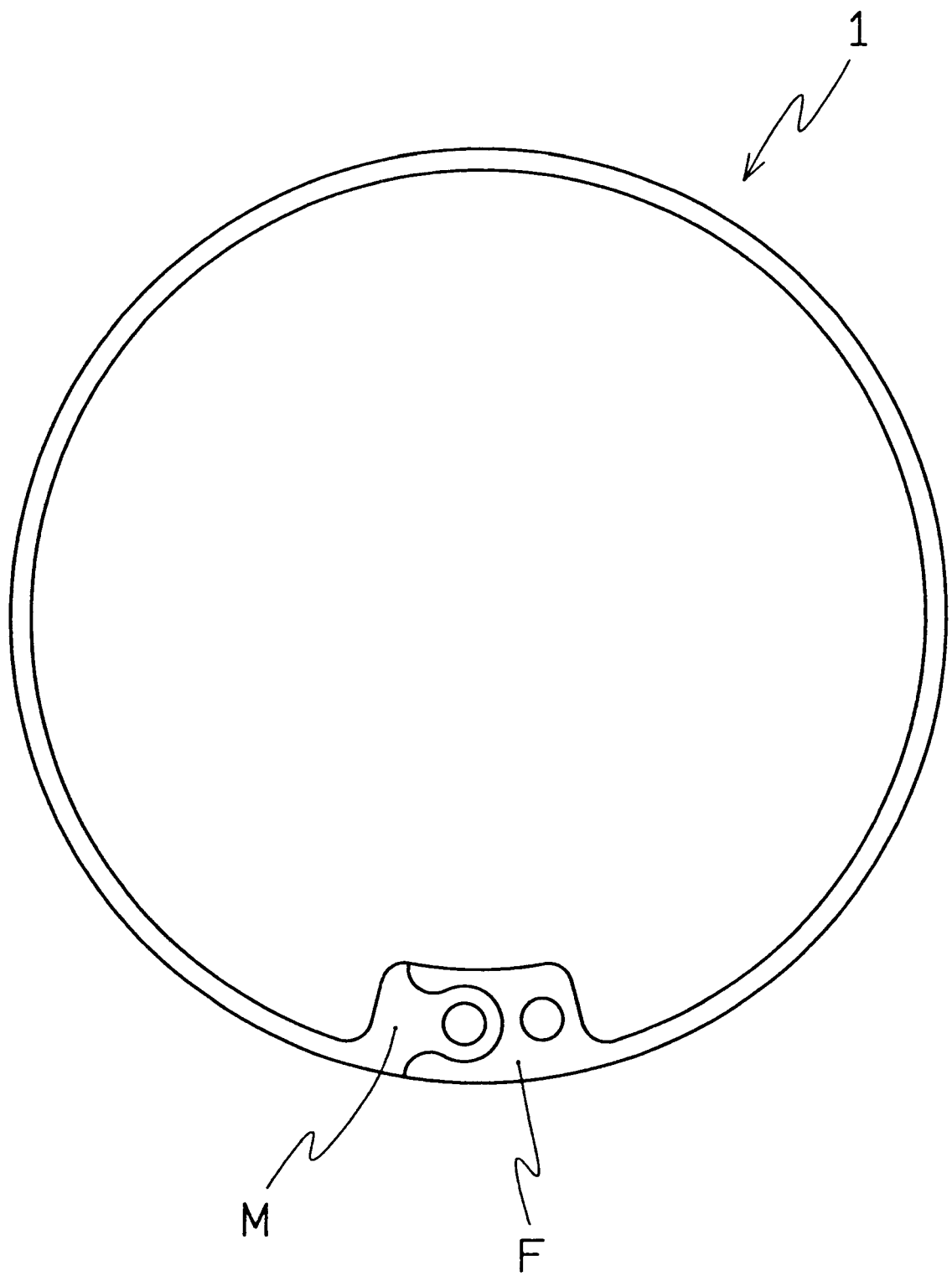
FIG. 4 is a plan view showing an engaged state of the ring of FIG. 3.

Referring to FIG. 1(a) and FIG. 1(b), a ring 1 of this embodiment is composed of a biocompatible material such as poly (methyl methacrylate) (PMMA), polypropylene (PP), hydrogel, fibronectin, polysulfone, chondroitin sulfate, a compound of hyaluronic acid, or similar compound, a biopolymer such as hydroxyethyl methacrylate, N-vinyl pyrrolidone, vinyl alcohol, or collagen, an elastomer such as silicone rubber, acrylic rubber, or their mixture or copolymer, a material such as polyethylene, vinyl chloride, poly (vinylidene fluoride), polyurethane, ethylene-vinyl acetate copolymer, siloxanyl styrene, similar material, and also a polymer such as polyurea, polyether, polyester, or copolysiloxane, a polymer such as polyacrylate or polymethacrylate, methyl methacrylate, styrene, methyl styrene, vinyl pyridine, similar copolymer, a copolymer such as N-alkyl, N,N-dialkyl acrylamide, or methacrylamide, or other shape memory material.

The ring 1 is partially cut off, that is, a so-called open ring, in which a male part M having a protrusion 5 is formed at one end of the cut section, and a female part F having a recess 10 complementary to the protrusion 5 is formed at other end. The male part M and female part F compose an engaging mechanism 2.

As the male part M and female part F engage with each other, a continuous ring form without cut section is formed.

Further, in this embodiment, since the supporting protrusion 5 is formed in the male part M, after engagement of the male part M and female part F, this supporting protrusion 5 contacts with the root of the female part F. As a result, a uniform tension (compressive load) is applied to the entire ring 1. In the case of the ring of the embodiment, after engagement of the male part M and female part F, when the ring diameter is contracted by 2 mm, a compressive load of about 250 mgf or more is obtained.

EMBODIMENT 2

Figure 9A:
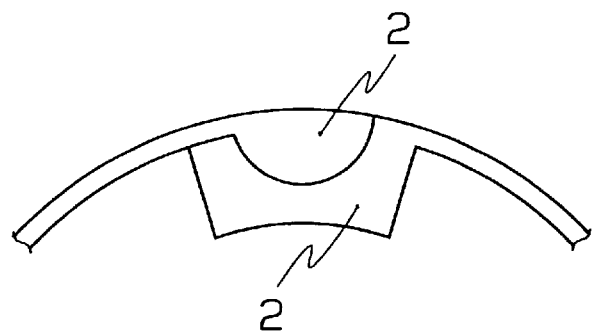
FIGS. 9(a) to 9(d) are partial plan views each showing another example of an engaged state of the ring of FIGS. 8(a) and 8(e)
Figure 9B:
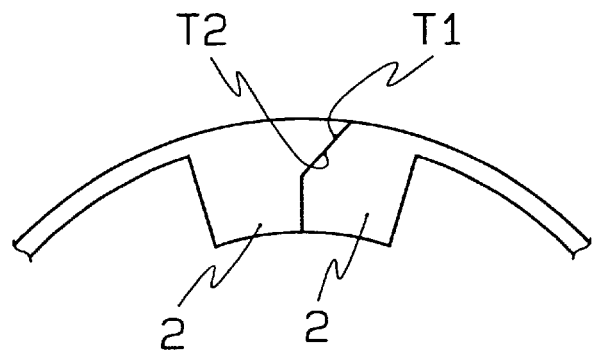
Figure 9C:
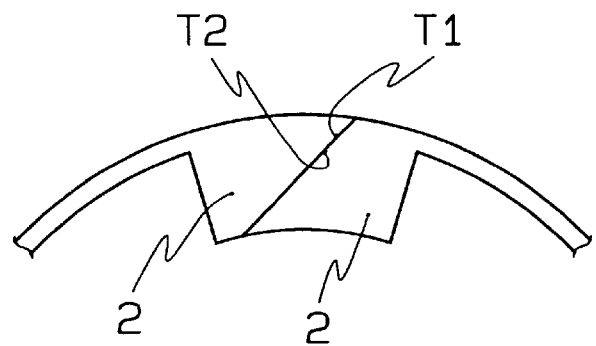
Figure 9D:
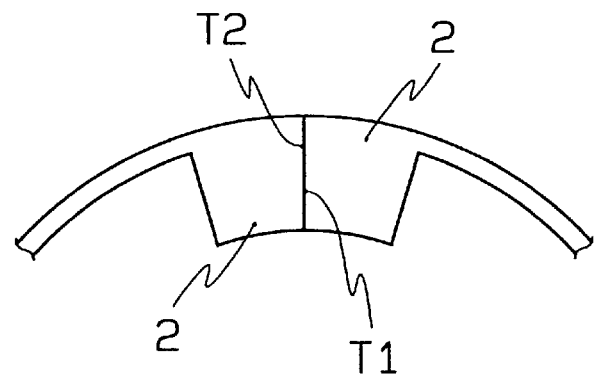
Figure 10A:
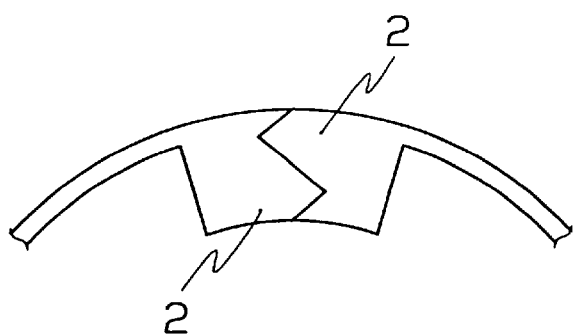
FIGS. 10(a) to 10(e) are partial plan views each showing still another example of an engaged state of the ring of FIGS. 8(a) to 8(e)
Figure 10B:
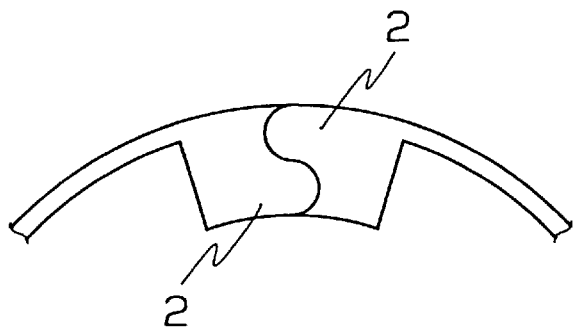
Figure 10C:
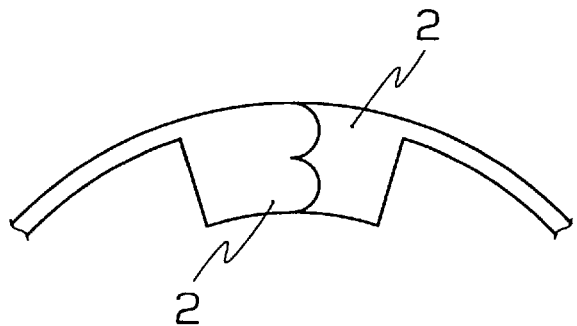
Figure 10D:
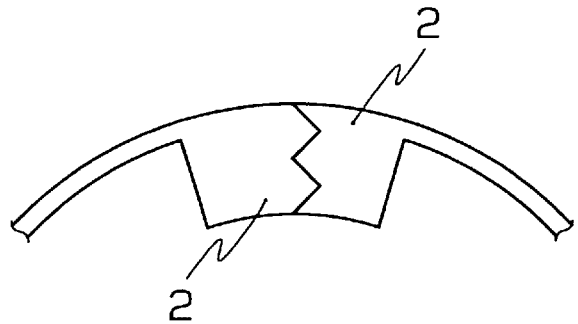
Figure 10E:
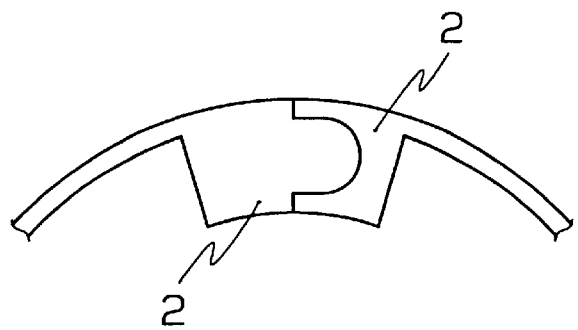
Figure 11A:
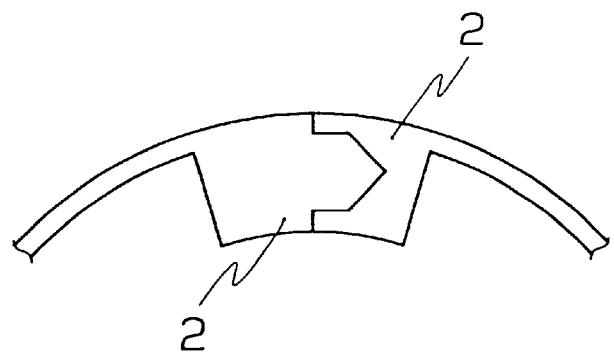
FIGS. 11(a) to 11(d) are partial plan views each showing yet another example of an engaged state of the ring of FIGS. 8(a) to 8(e)
Figure 11B:
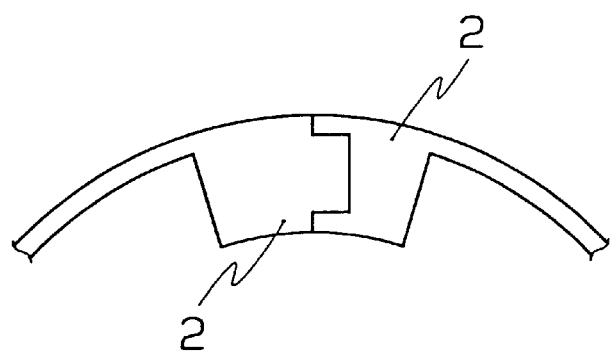
Figure 11C:
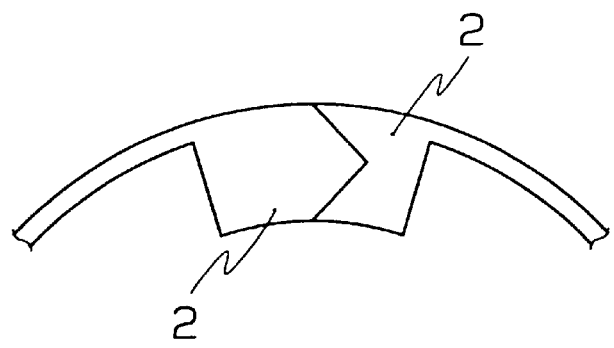
Figure 11D:
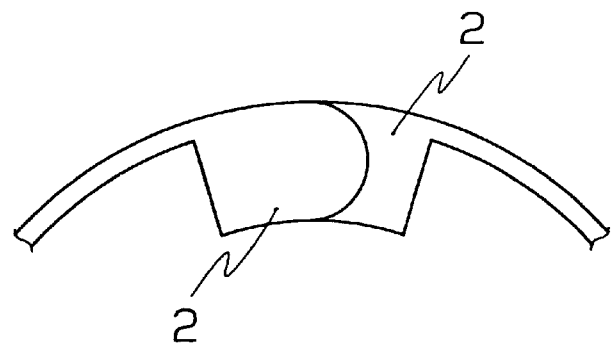
Figure 12A:
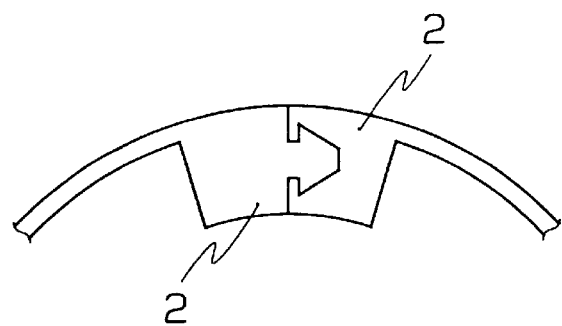
FIG. 12(a) to 12(e) are partial plan views each showing yet another example of an engaged state of the ring of FIGS. 8(a) to 8(e)
Figure 12B:
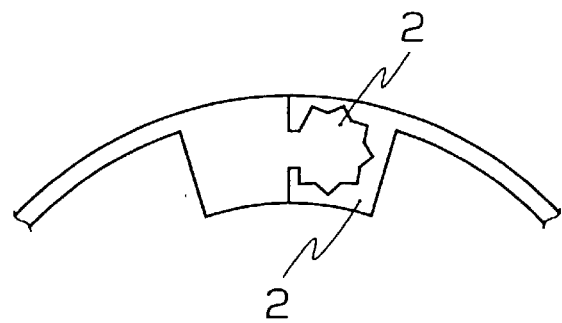
Figure 12C:
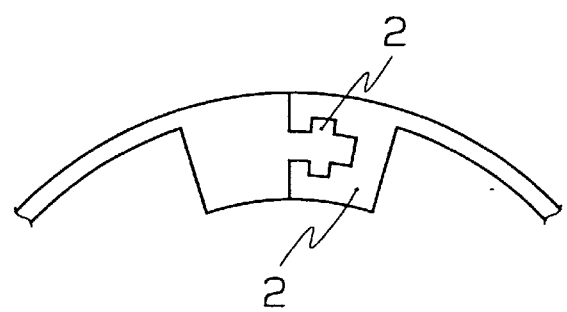
Figure 12D:
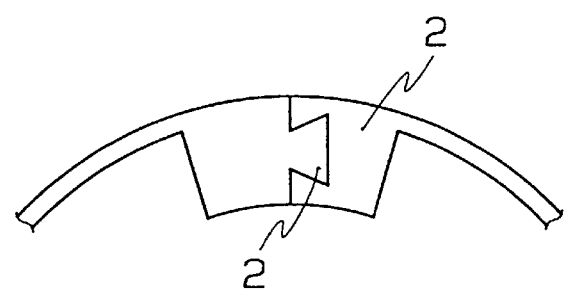
Figure 12E:
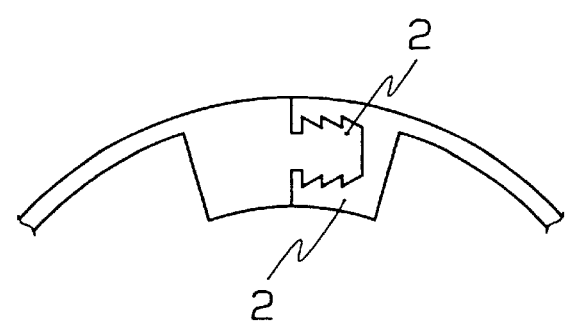
Figure 13A:
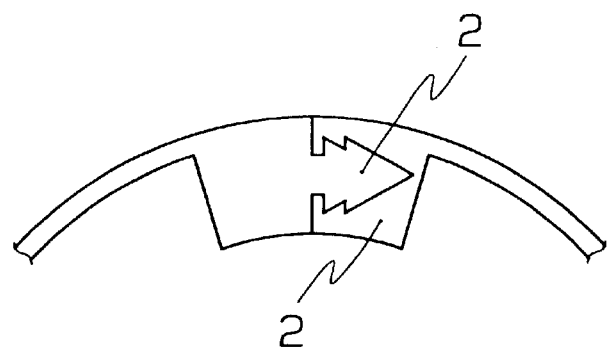
FIGS. 13(a) to 13(d) are partial plan view each showing yet another example of an engaged state of the ring of FIGS. 8(a) to 8(e)
Figure 13B:
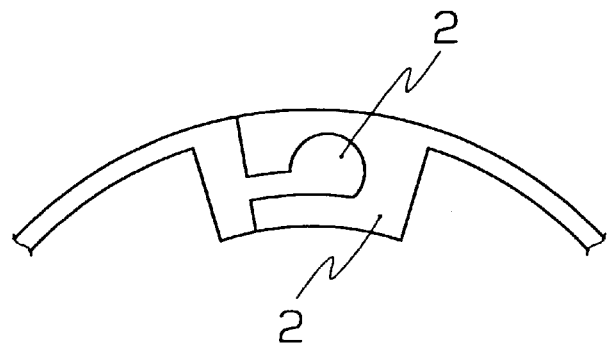
Figure 13C:
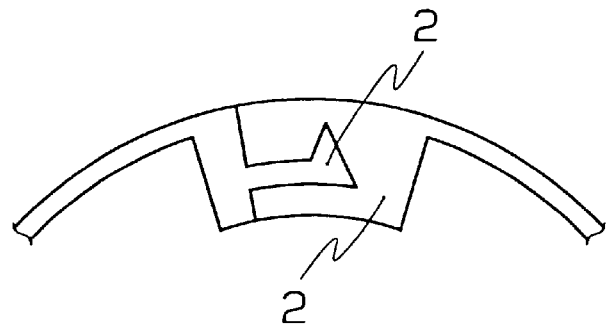
Figure 13D:
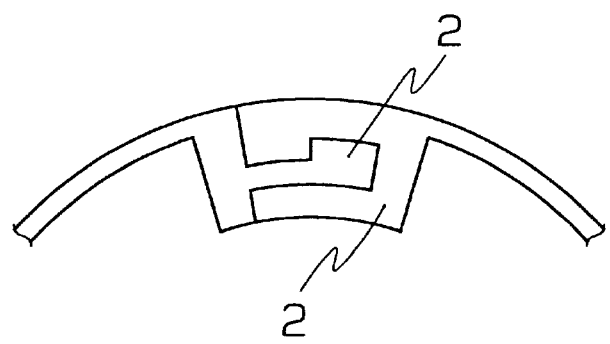
Figure 14A:
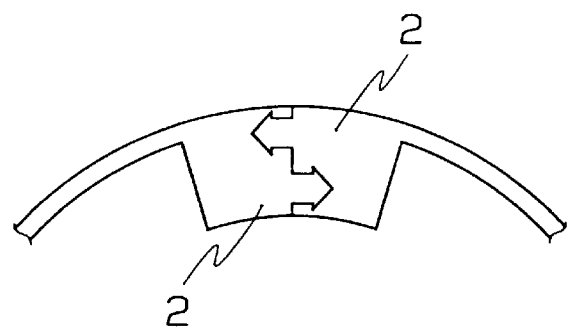
FIGS. 14(a) to 14(e) are partial plan views each showing yet another example of an engaged state of the ring of FIGS. 8(a) to 8(e)
Figure 14B:
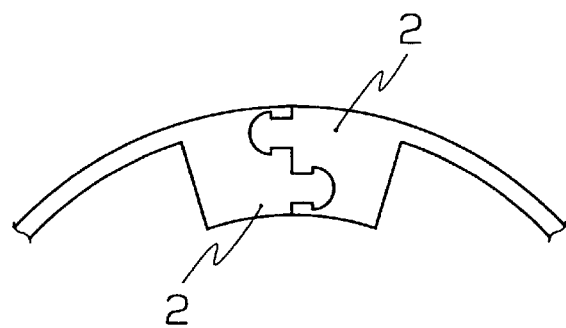
Figure 14C:
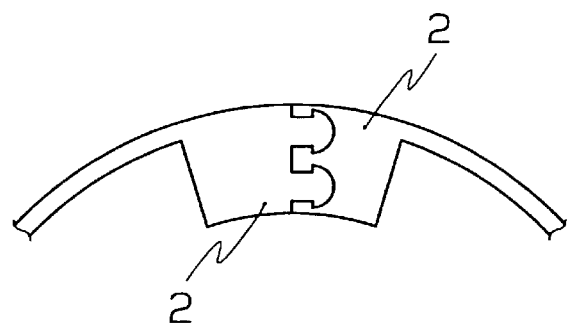
Figure 14D:
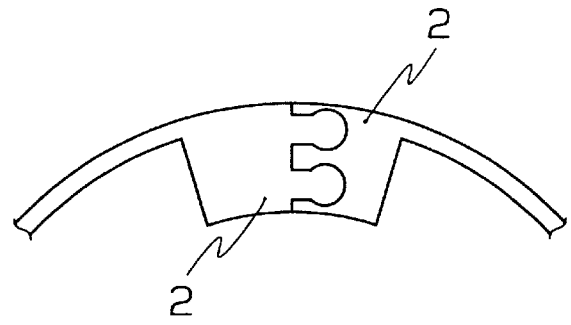
Figure 14E:
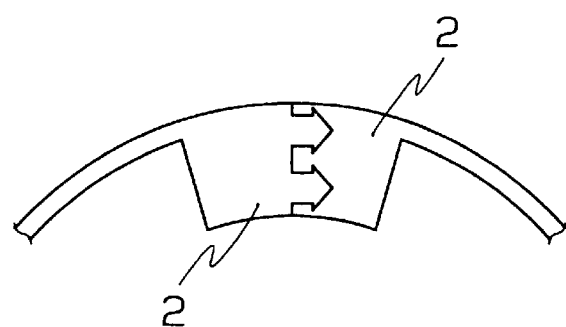
Figure 15A:
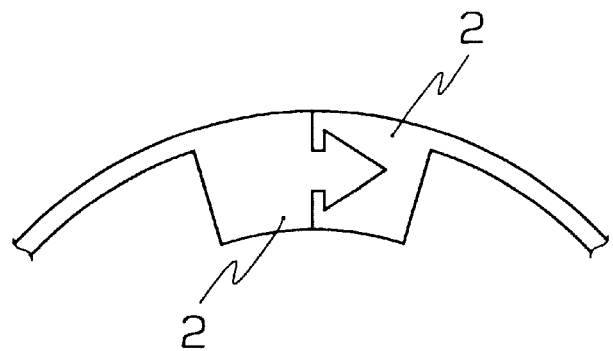
FIGS. 15(a) to 15(d) are partial plan views each showing yet another example of an engaged state of the ring of FIGS. 8(a) to 8(e)
Figure 15B:
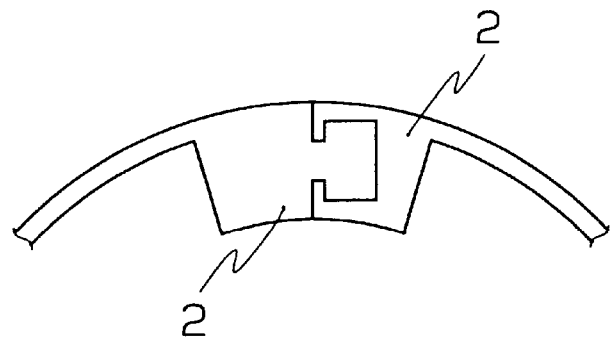
Figure 15C:
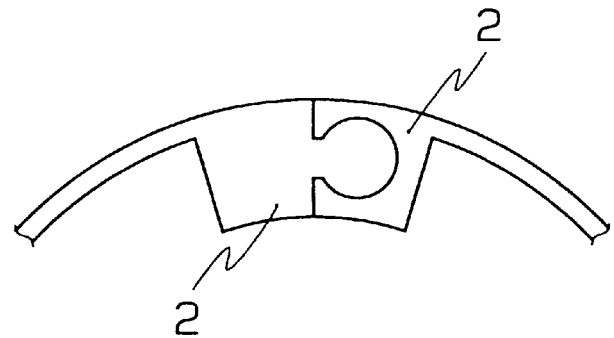
Figure 15D:
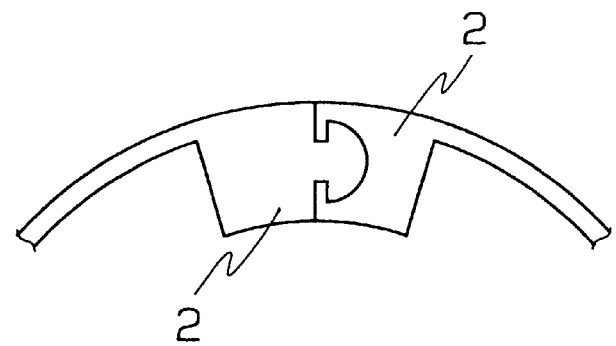
Figure 16A:
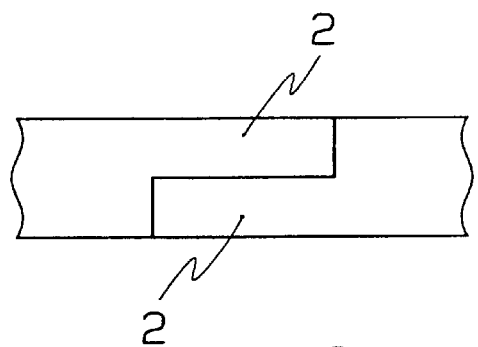
FIGS. 16(a) to 16(e) are partial side views each showing one example of an engaged state of the ring of FIGS. 8(a) to 8(e)
Figure 16B:
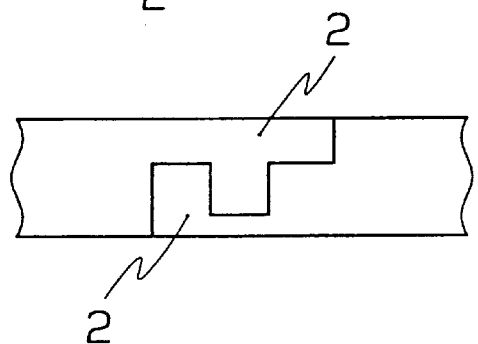
Figure 16C:
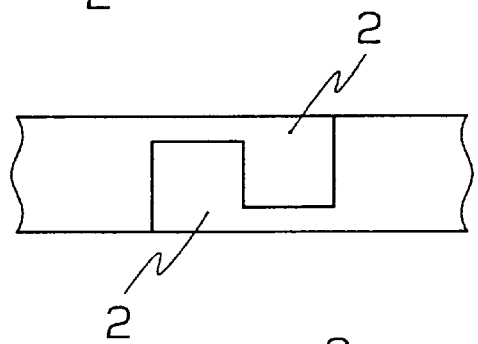
Figure 16D:
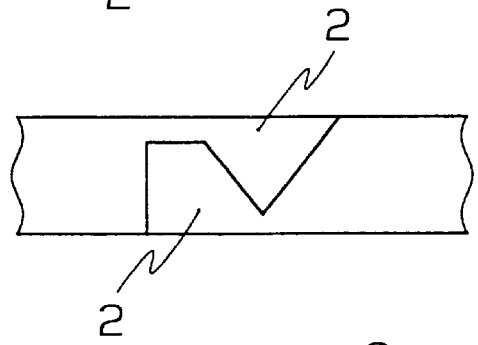
Figure 16E:
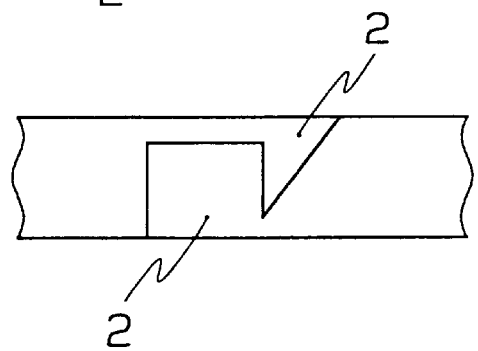
Figure 17A:
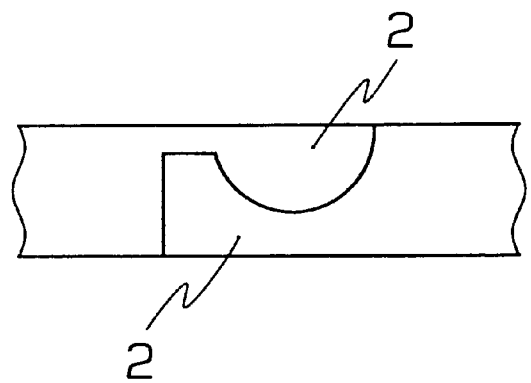
FIGS. 17(a) to 17(d) are partial side views each showing another example of an engaged state of the ring of FIGS. 16(a) to 16(e)
Figure 17B:
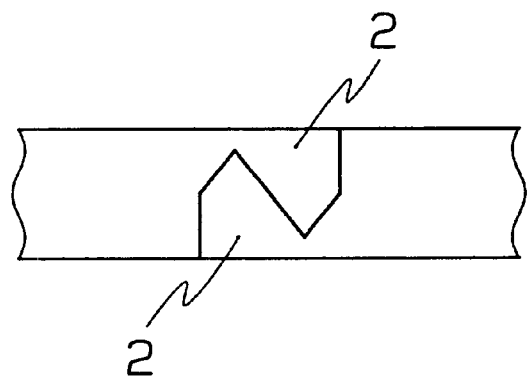
Figure 17C:
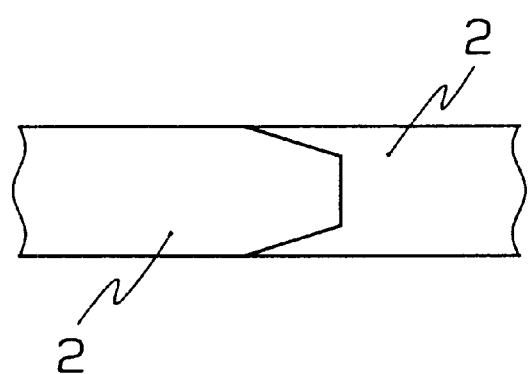
Figure 17D:
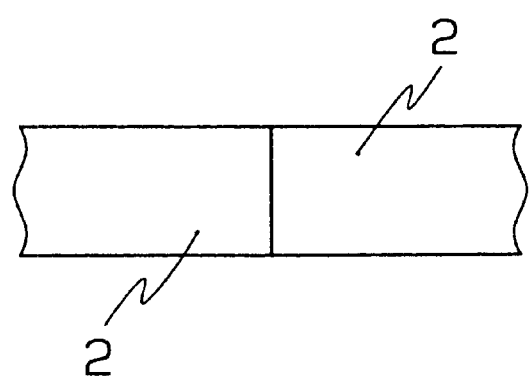
Figure 18A:
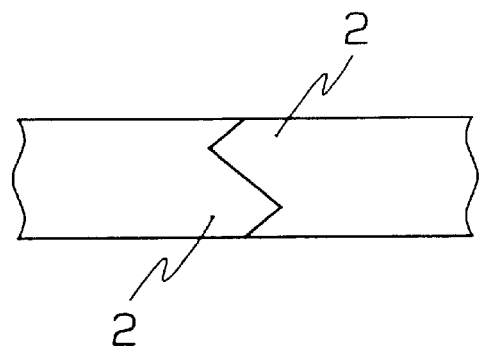
FIGS. 18(a) to 18(e) are partial side views each showing still another example of an engaged state of the ring of FIGS. 16(a) to 16(e)
Figure 18B:
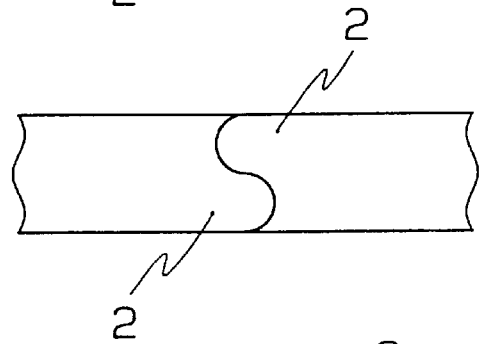
Figure 18C:
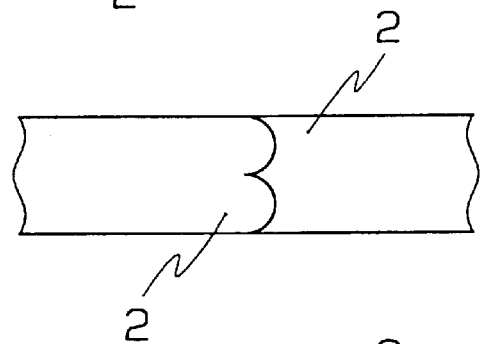
Figure 18D:
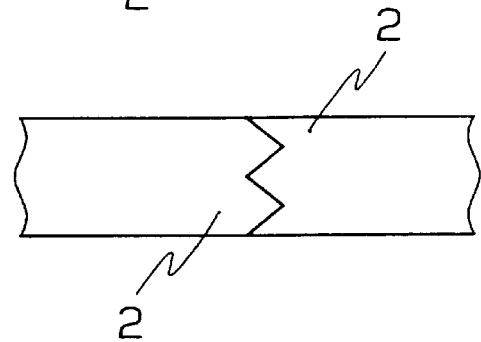
Figure 18E:
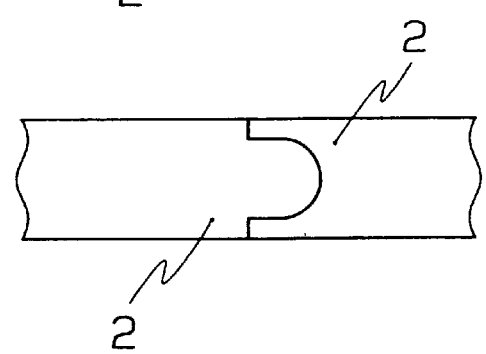
Figure 19A:
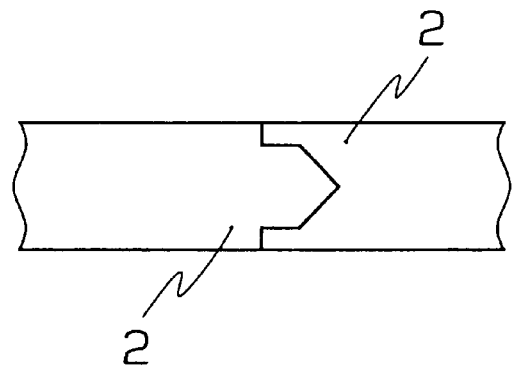
FIGS. 19(a) to 19(d) are partial side views each showing yet another example of an engaged state of the ring of FIGS. 16(a) to 16(e)
Figure 19B:
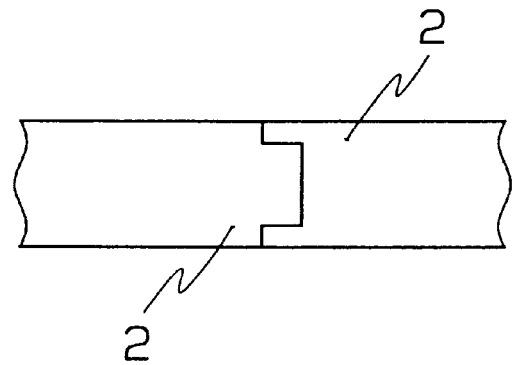
Figure 19C:
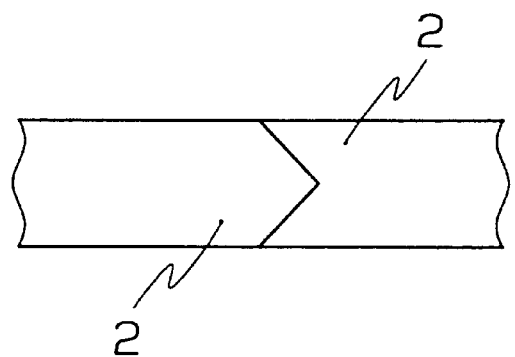
Figure 19D:
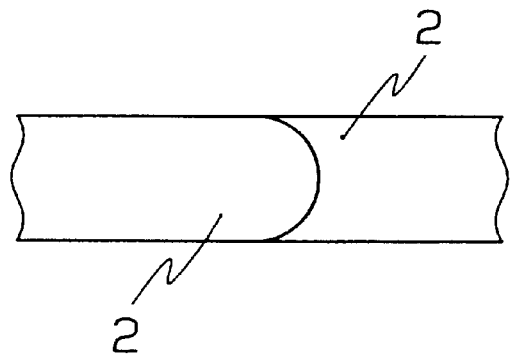
Figure 20A:
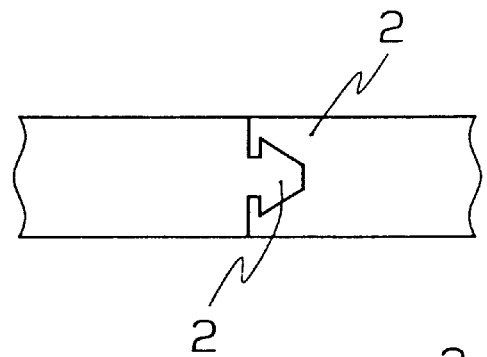
FIGS. 20(a) to 20(e) are partial side views each showing yet another example of an engaged state of the ring of FIGS. 16(a) to 16(e)
Figure 20B:
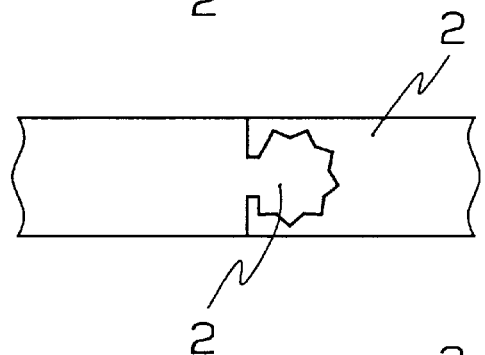
Figure 20C:
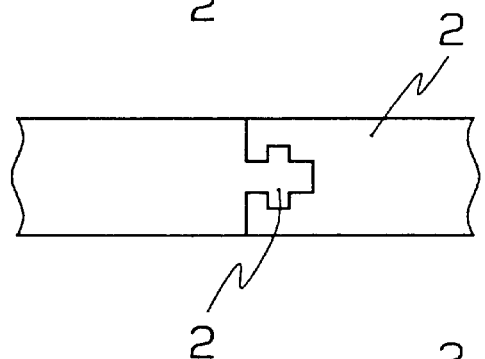
Figure 20D:
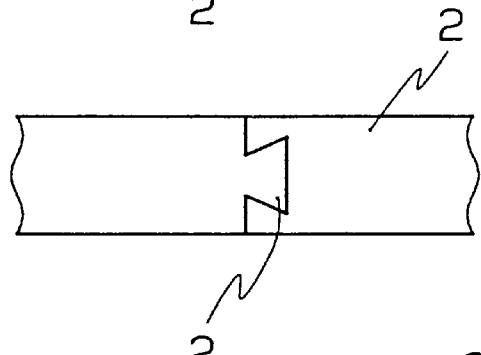
Figure 20E:
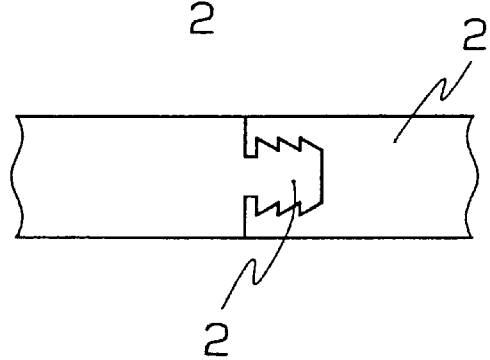
Figure 21A:
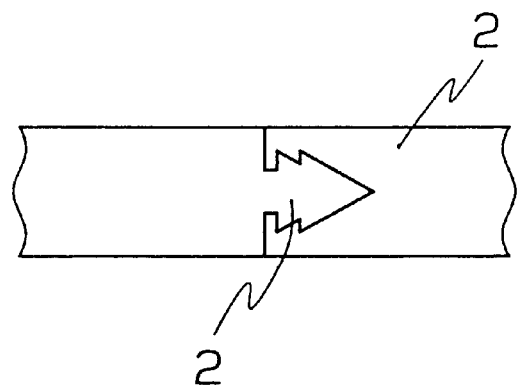
FIGS. 21(a) to 21(d) are partial side views each showing yet another example of an engaged state of the ring of FIGS. 16(a) to 16(e)
Figure 21B:
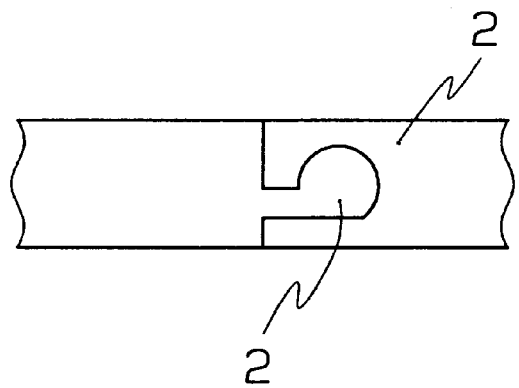
Figure 21C:
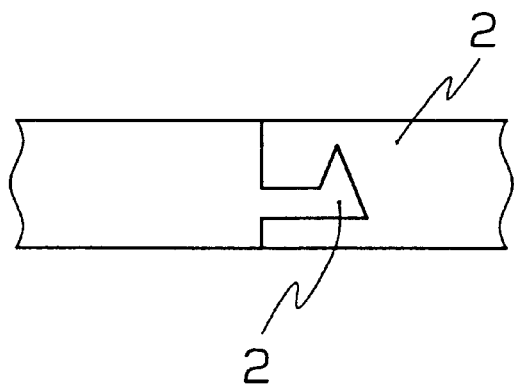
Figure 21D:
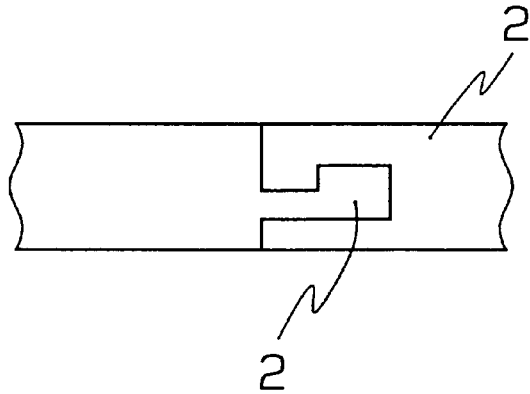
Figure 22A:
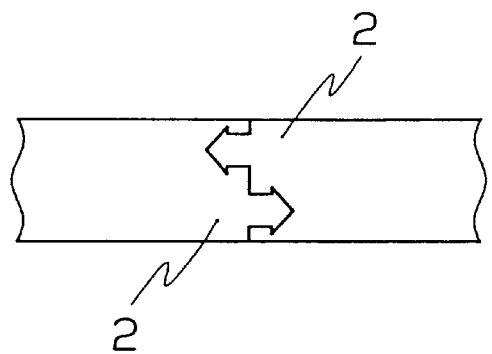
FIGS. 22(a) to 22(e) are partial side views each showing yet another example of an engaged state of the ring of FIGS. 16(a) to 16(e)
Figure 22B:
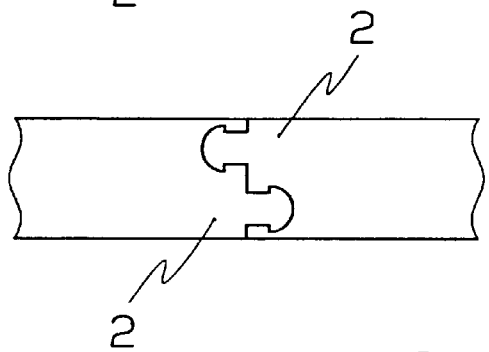
Figure 22C:
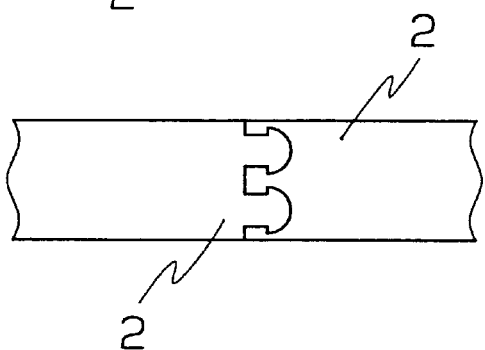
Figure 22D:
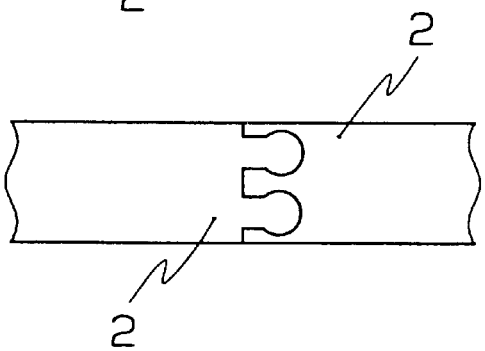
Figure 22E:
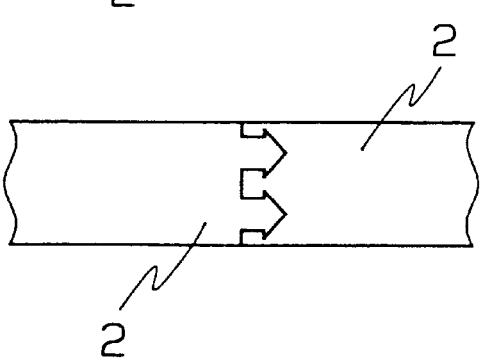

The ring 1 of this embodiment is an intraocular ring in a constitution as shown in any one of partial plan views of FIG. 8 (a), FIG. 9 (c) and FIG. 9(d), and a side view in FIG. 17(d), and when inserted into the capsule, the both ends of the cut ring are joined to form a continuous shape.

The material of the ring 1 of this embodiment is same as that of the ring of embodiment 1.

In the case of the ring of this embodiment, too, after joining the both ends of the cut ring, when the ring diameter is contracted by 2 mm, a compressive load of about 250 mgf or more is obtained.

EMBODIMENT 3

The ring 1 of the embodiment, as shown in FIG. 9(b) and FIG. 9(c) and FIG. 17(c), has tapers T1, T2 formed at both ends of the ring 1. In this constitution, it is preferred as deviation of abutting position of the tapers T1 and T2 is prevented. The material of the ring 1 of this embodiment is same as that of the ring of embodiment 1. Also the case of the ring of this embodiment, after joining the tapers T1 and T2, when the ring diameter is contracted by 2 mm, a compressive load of about 250 mgf or more is obtained.

EMBODIMENT 4

Figure 5:
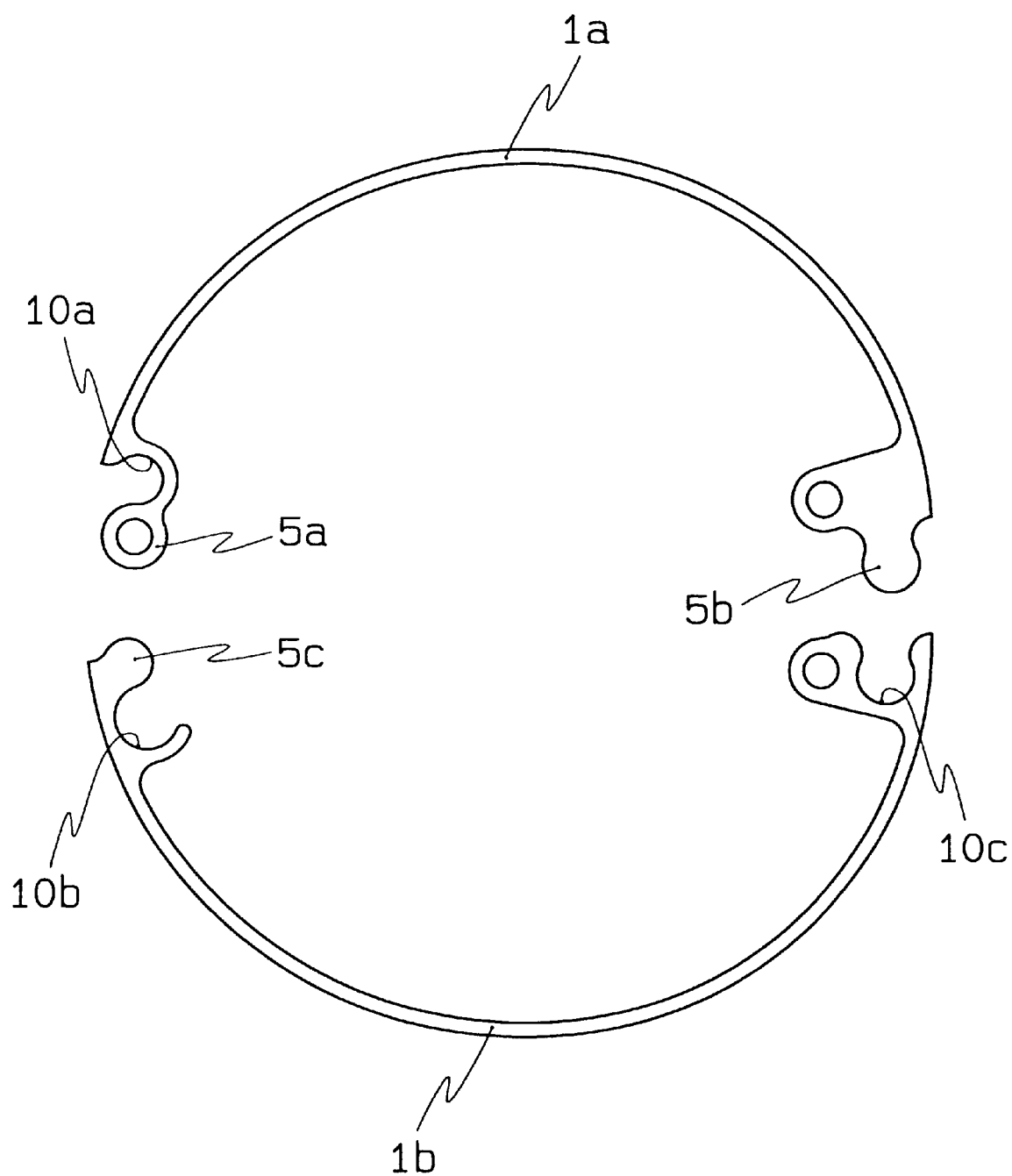
FIG. 5 is a plan view showing another embodiment of a ring of the present invention in which the ring is composed of two parts.

The ring 1 of this embodiment is composed of part 1a and part 1b (see FIG. 5).

In the part 1a and part 1b, in order that arbitrary adjacent parts may be engaged with each other in a male-female structure, a first protrusion 5a and a first recess 10a positioned at the root of the first protrusion 5a are formed at one end of the part 1a, while a second protrusion 5b is formed at other end. Further, at one end of the part 1b, a third protrusion 5c to be fitted into the first recess 10a, and a second recess 10b positioned at the root of the third protrusion 5c are formed, while a third recess 10c to be fitted with the second protrusion 5b is formed at other end.

Figure 6:
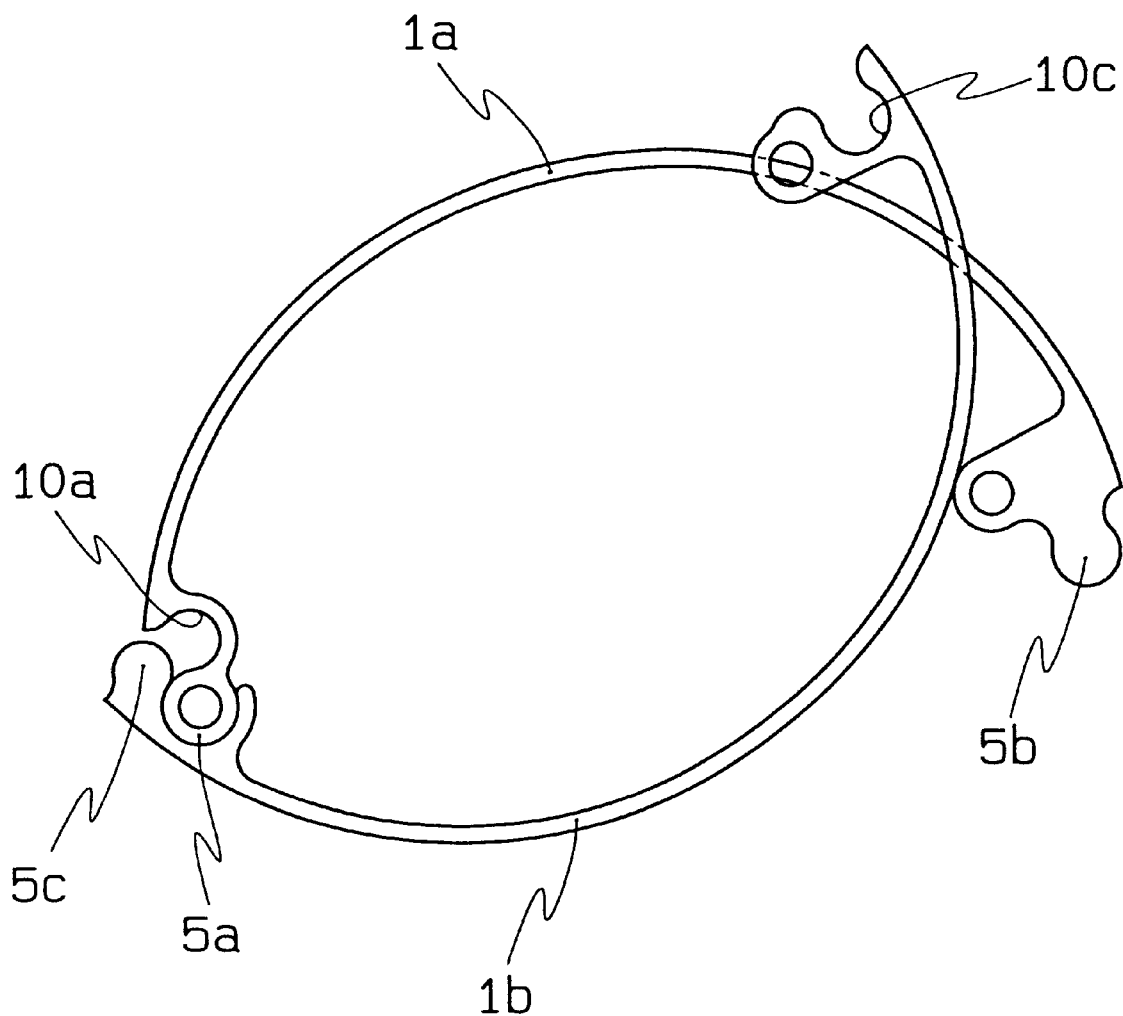
FIG. 6 is a plan view showing a state of the ring of FIG. 5 in which the two part is swingably engaged with each other.
Figure 7:
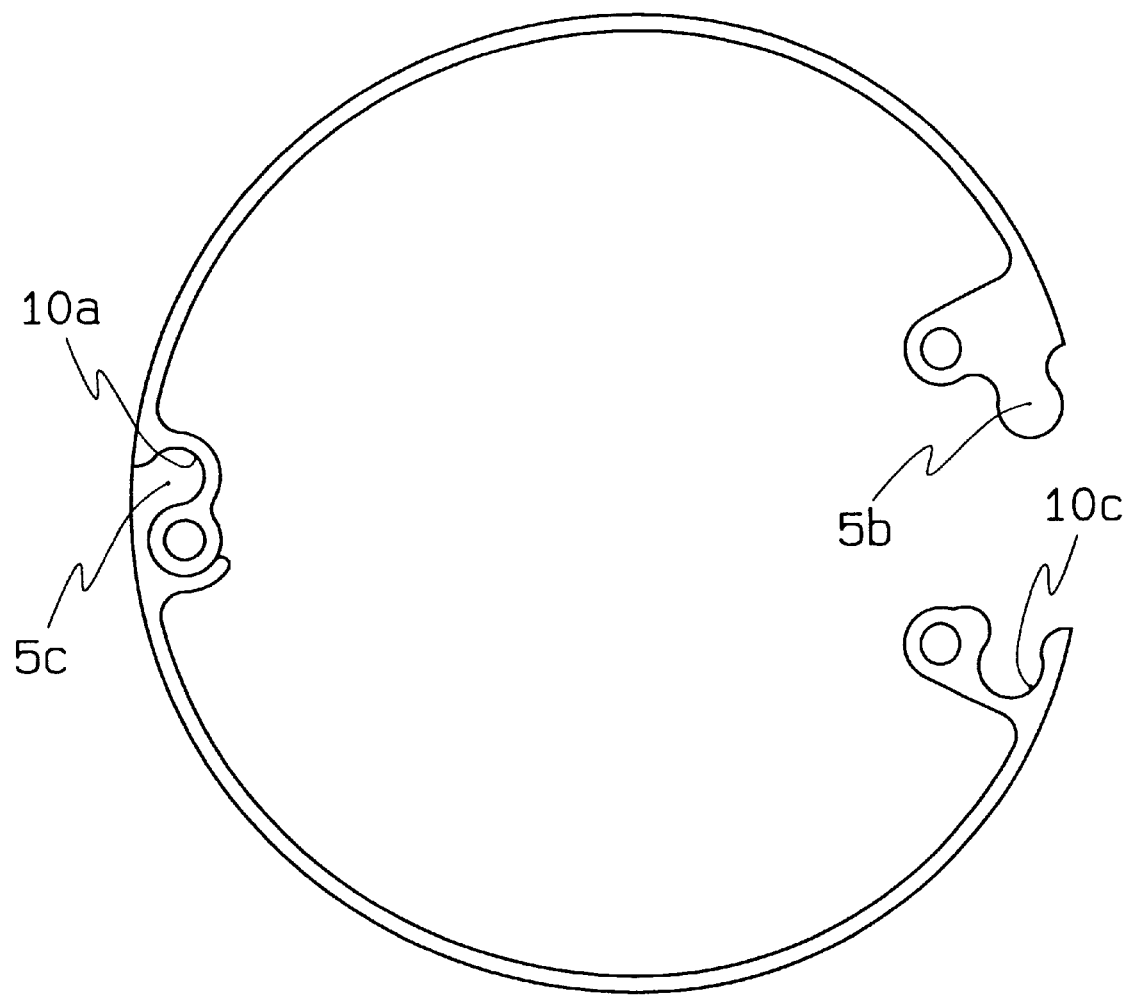
FIG. 7 is a plan view showing a state of the ring of FIG. 5 serving as an open ring.
Figure 8A:
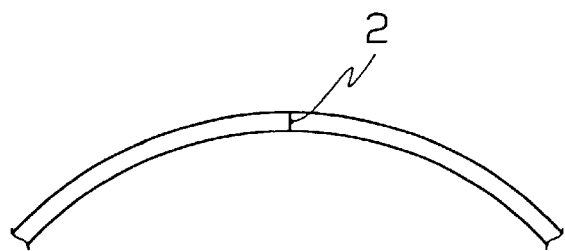
FIGS. 8(a) to 8(e) show partial plan views, each showing an example of an engaged state of the ring of the present invention.
Figure 8B:
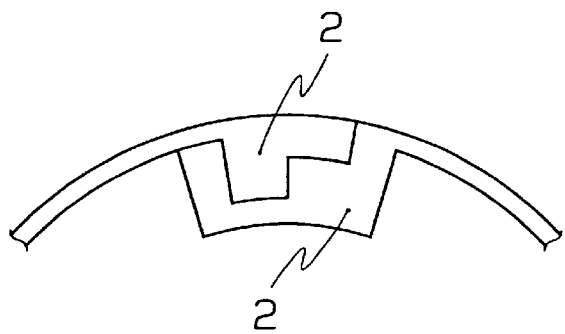
Figure 8C:
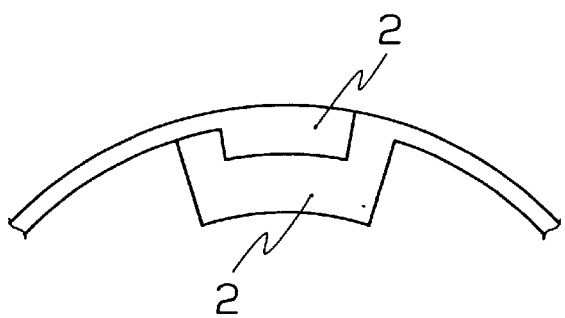
Figure 8D:
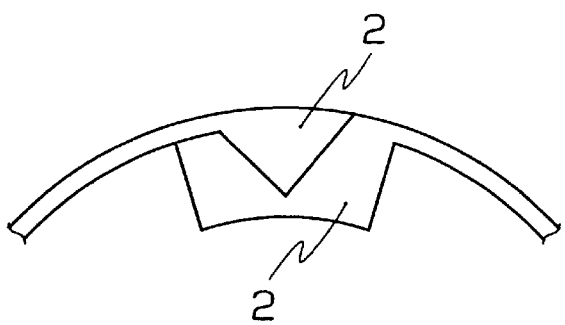
Figure 8E:
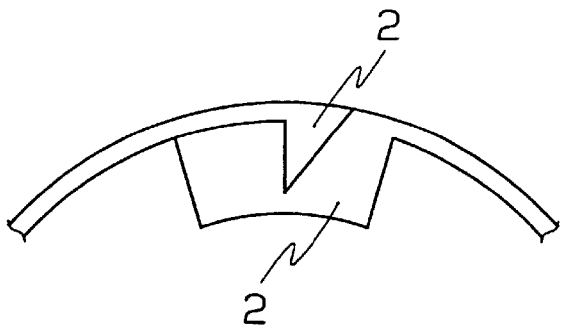

The ring 1 of the embodiment is inserted into the capsule (see FIG. 6), first in a state of fitting the first protrusion 5a into the second recess 10b by means of jig such as forcept. When the third protrusion 5c is fitted into the first recess 10a, a tension is applied to the ring 1. In this state, when the sitting position in the capsule is determined, the second protrusion 5b is fitted into the third recess 10c. The material of the ring 1 of this embodiment is same as that of the ring of embodiment 1. Also the case of the ring of this embodiment, after fitting the first protrusion 5a into the second recess 10b, fitting the third protrusion 5c into the first recess 10a, and fitting the second protrusion 5b into the third recess 10c, when the ring diameter is contracted by 2 mm, a compressive load of about 250 mgf or more is obtained.

The ring of the invention is a so-called open ring with one or two or more cut sections. In the foregoing embodiments, the engaging or joining mechanism of cut sections is explained by referring to the drawings, but it is not limited to the illustrated engaging and joining mechanisms.

Incidentally, by using therapeutics, including ocular hypotensor such as distigmine bromide, carteolol chloride or timolol maleate, cataract remedy such as pyrenoxin or glutathione, ocular infection remedy such as aciclovir, idoxuridine, oxytetracycline hydrochloride, ofloxacin, sulbenicillin sodium, cefmenoxime hydrochloride, tobramycin, micronomycin hydrosulfate or pimaricin, or antiinflammatory agents such as dexamethasone sodium phosphate, fluorometholone, metamethasone sodium phosphate, indomethacin or pranoprofen, antifungal agent such as griseofulvin, antibacterial agent such as gentamycin sulfate, antiviral agent such as vidarabine, aciclovir or didanosine, and diagnostic agent such as fluorescein sodium, when the surface of the ring (the contact surface of the ring and the lenticular capsule) of the invention is coated, or when mixed in the material of the ring, and it worn in the capsule, a sustained-release effect of the drug is obtained.

EMBODIMENT 5

Figure 24:
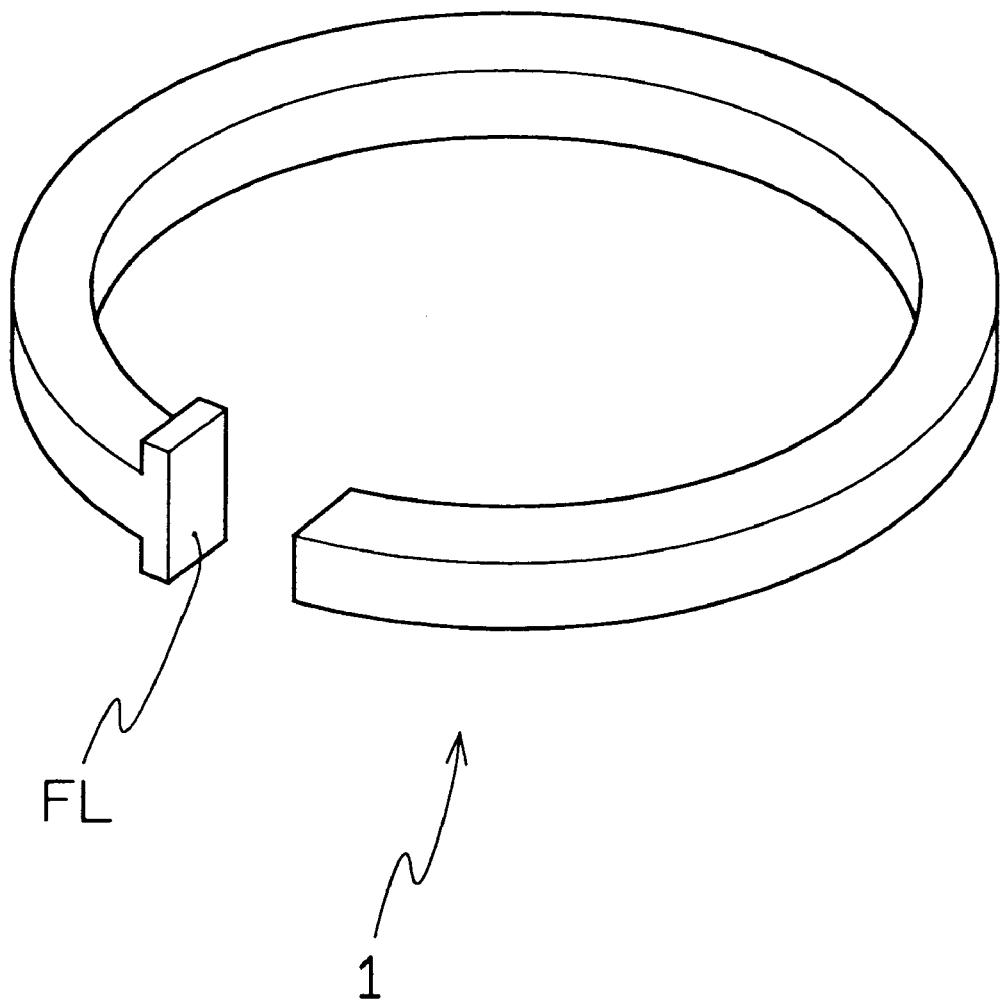
FIG. 24 is a perspective view showing an example of still another embodiment of a ring of the present invention.
Figure 25:
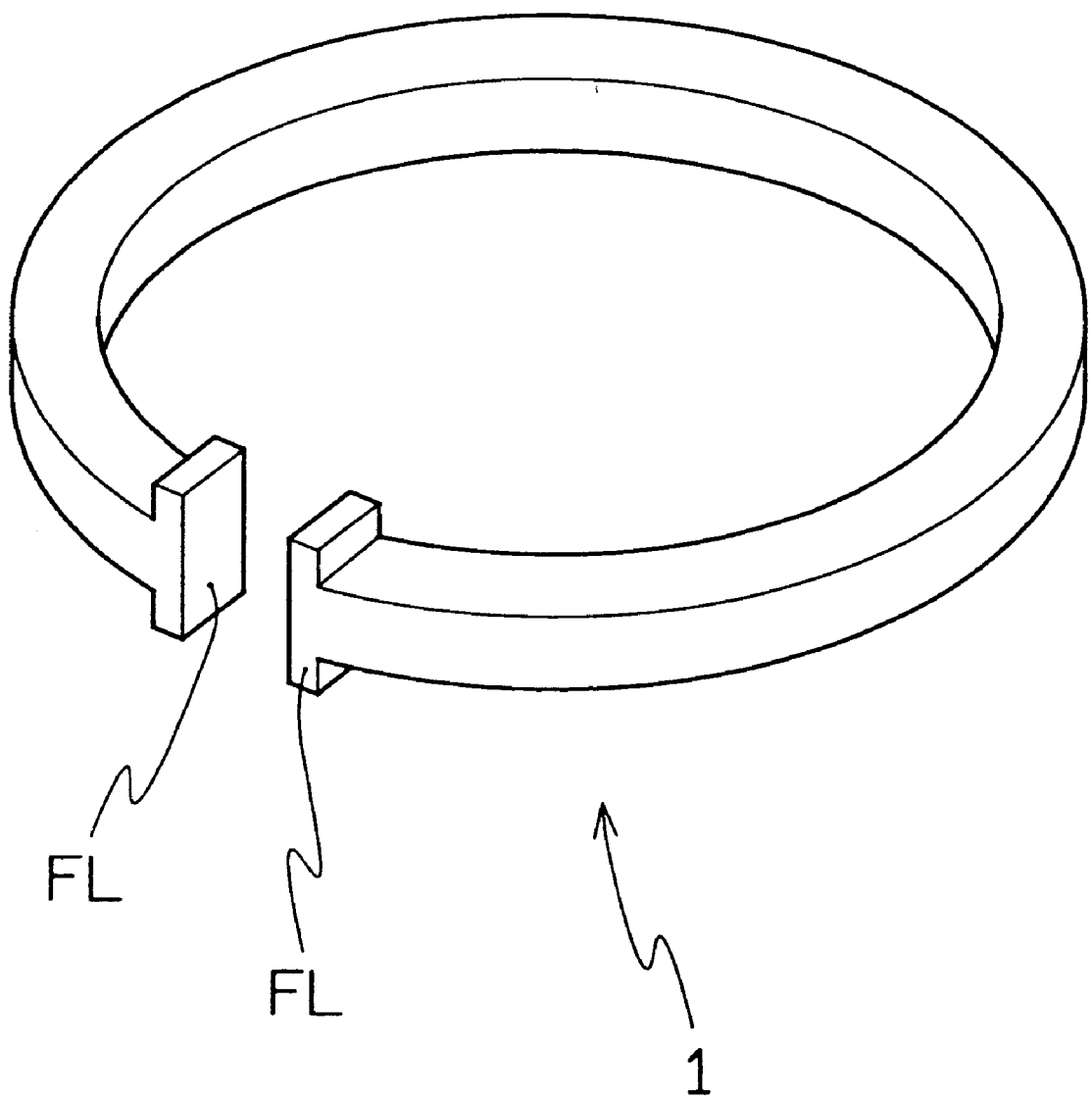
FIG. 25 is a perspective view showing another example of the ring of FIG. 24.
Figure 26:
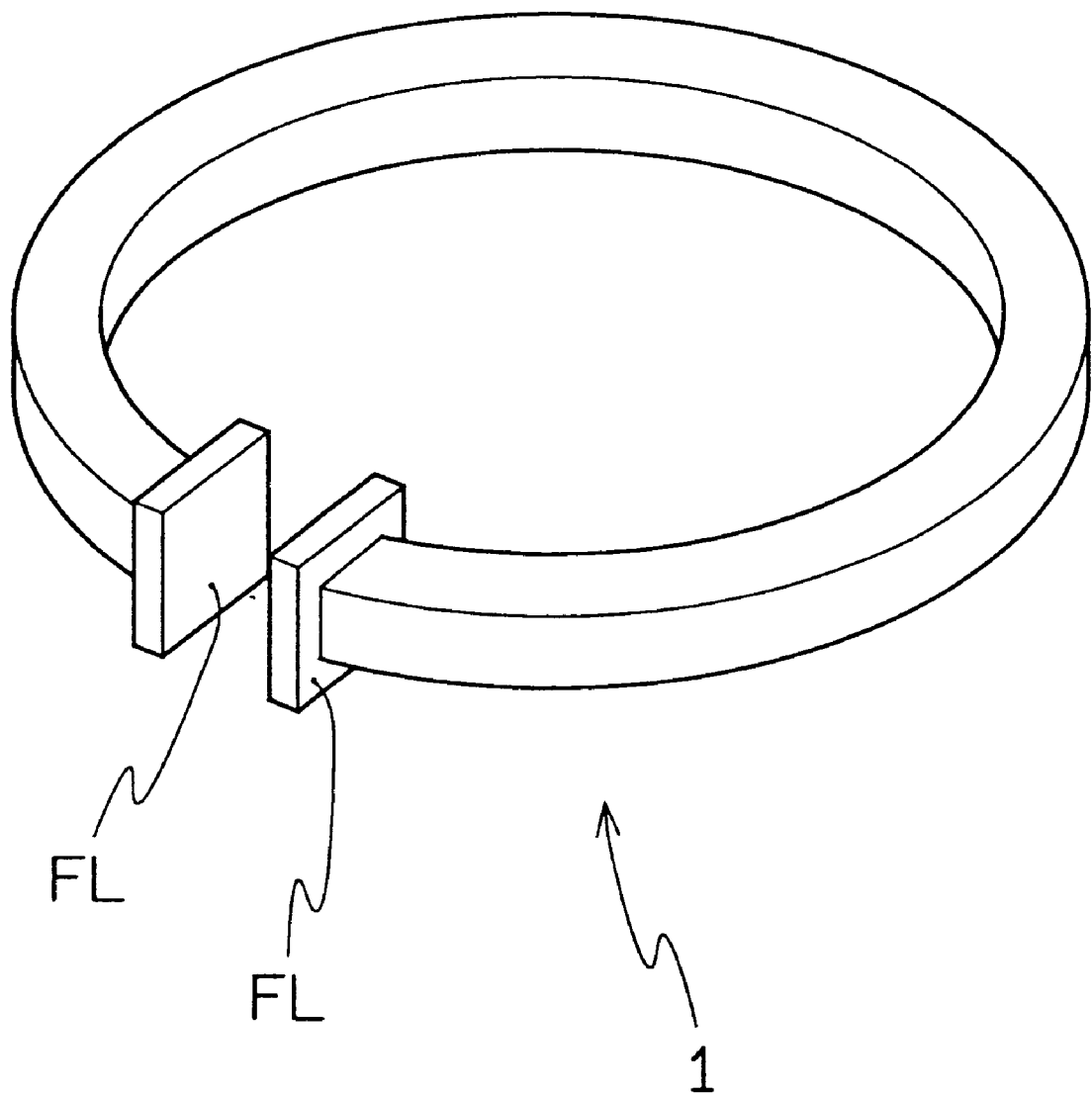
FIG. 26 is a perspective view showing still another example of the ring of FIG. 24.
Figure 27A:
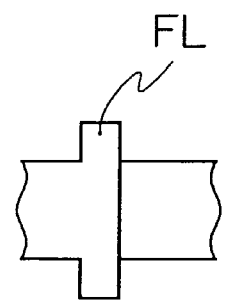
FIGS. 27(a) to 27(e) are partial side views each showing yet another example of the ring of FIGS. 24 to 26.
Figure 27B:
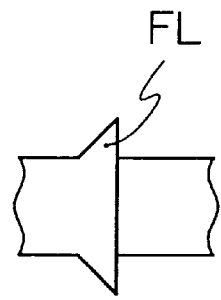
Figure 27C:
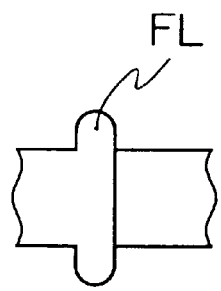
Figure 27D:
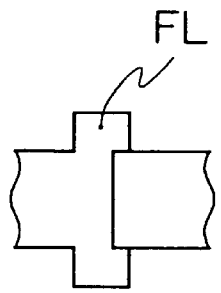
Figure 27E:
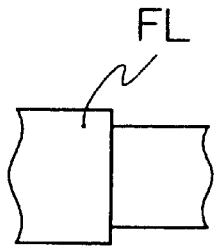
Figure 28A:
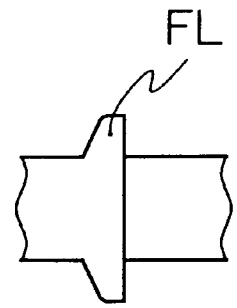
FIGS. 28(a) to 28(d) are partial side views showing yet another example of the ring of FIGS. 24 to 26.
Figure 28B:
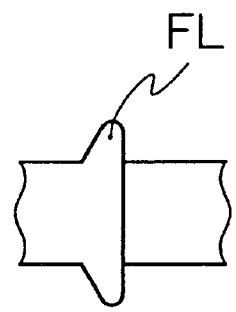
Figure 28C:
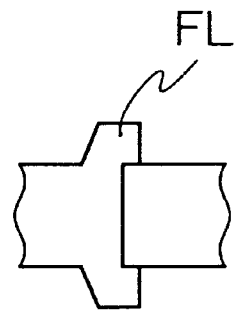
Figure 28D:
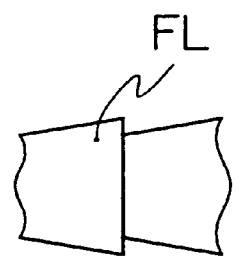
Figure 29A:
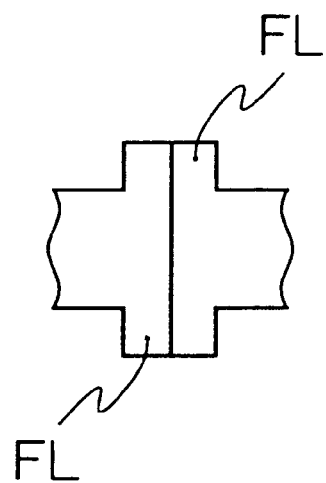
FIGS. 29(a) to 29(c) are partial side views each showing yet another example of the ring of FIGS. 24 to 26.
Figure 29B:
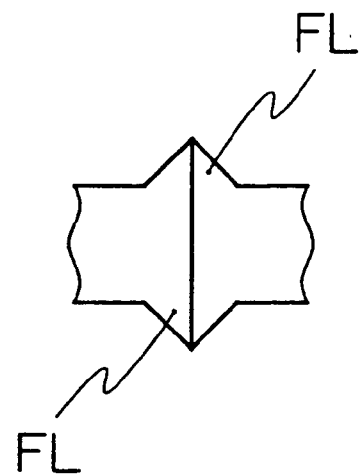
Figure 29C:
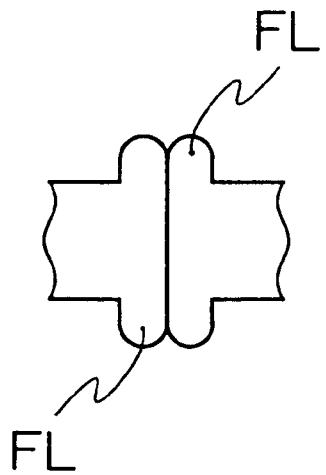
Figure 30A:
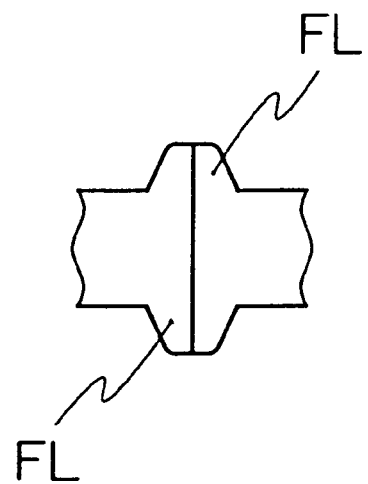
FIGS. 30(a) to 30(c) are partial side views each showing yet another example of the ring of FIGS. 24 to 26.
Figure 30B:
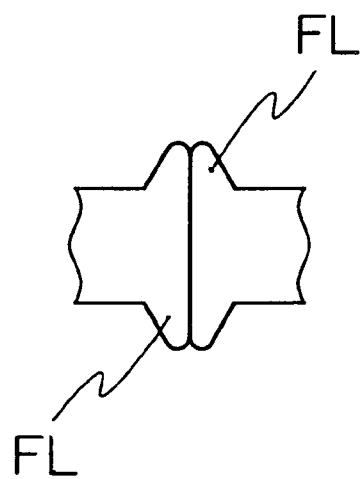
Figure 30C:
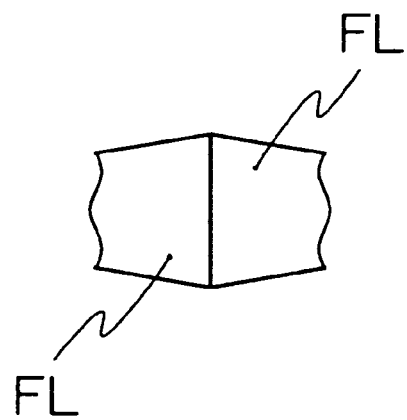
Figure 31:
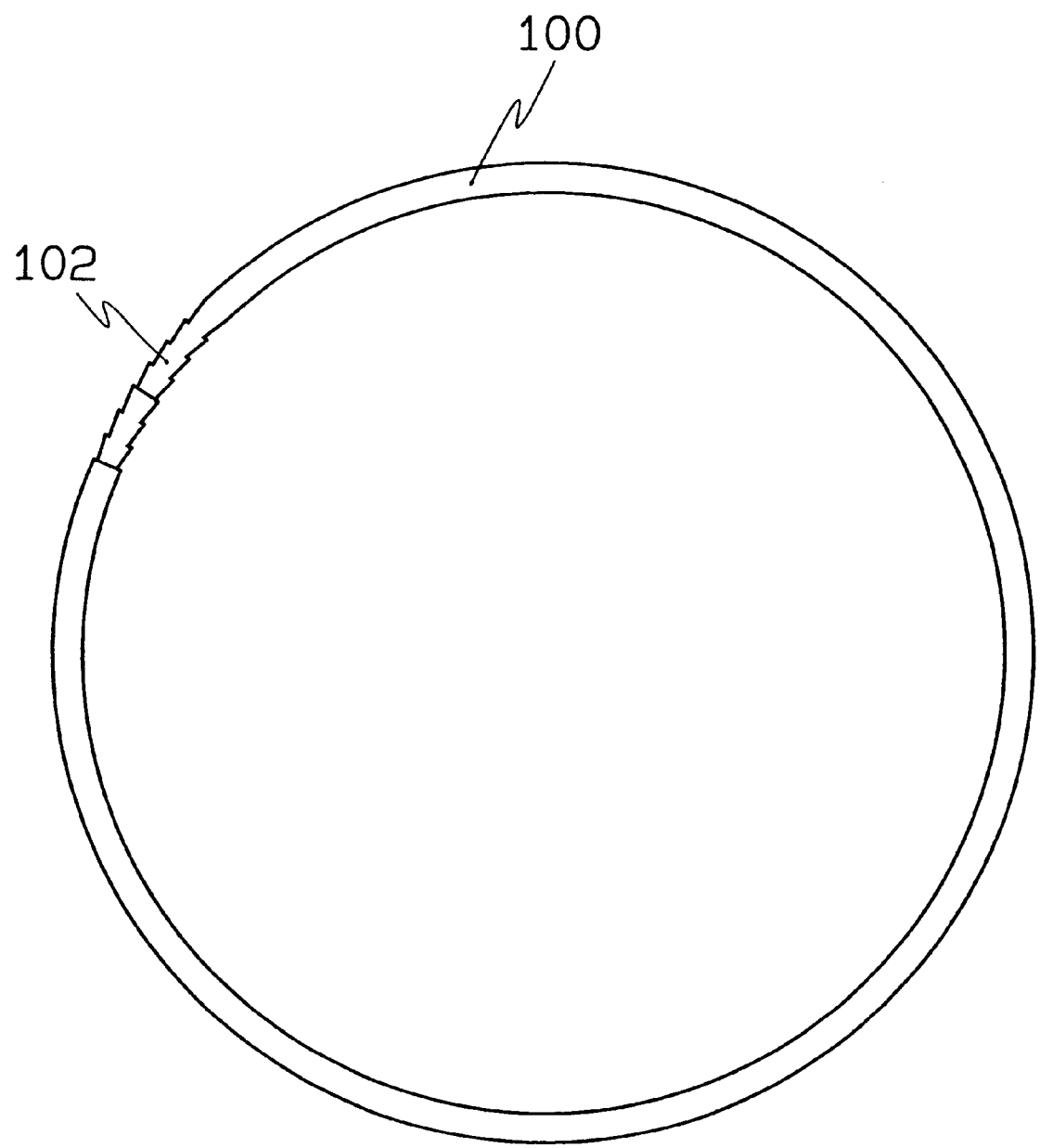
FIG. 31 is a plan view showing one example of conventional ring.
Figure 32:
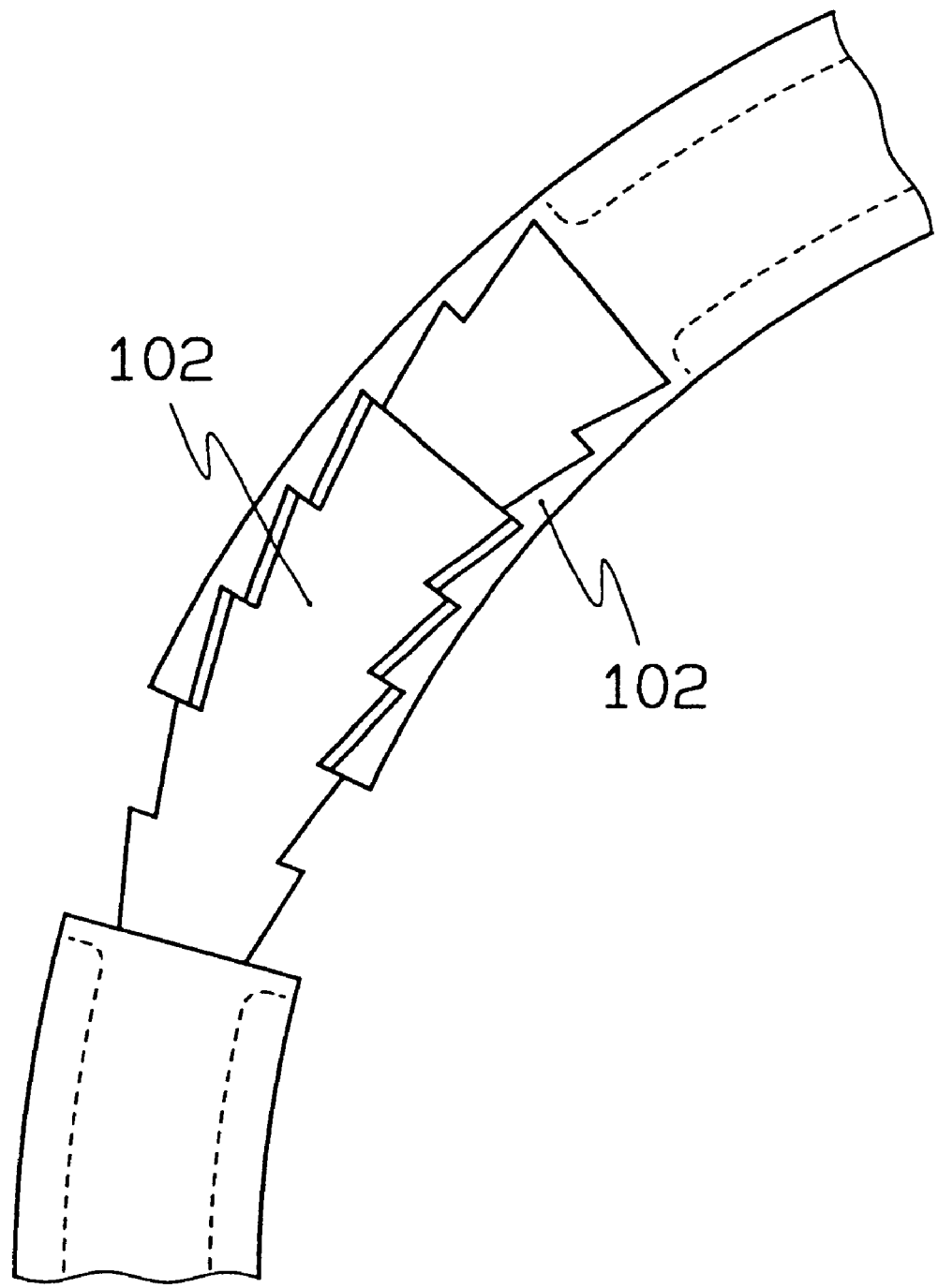
FIG. 32 is a partially enlarged view of the ring of FIG. 31.
Figure 33:
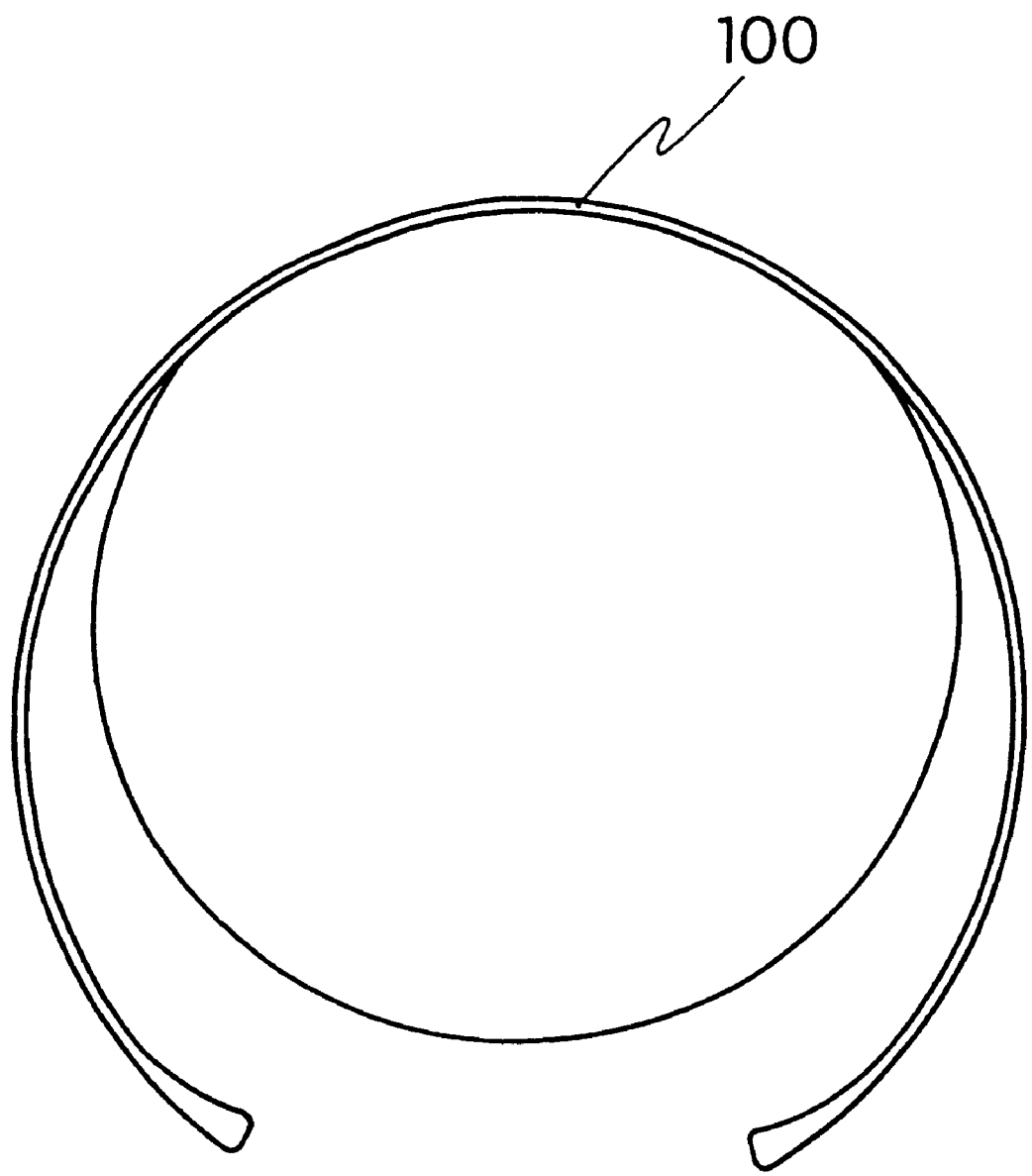
FIG. 33 is a plan view showing another example of conventional ring.
Figure 34:
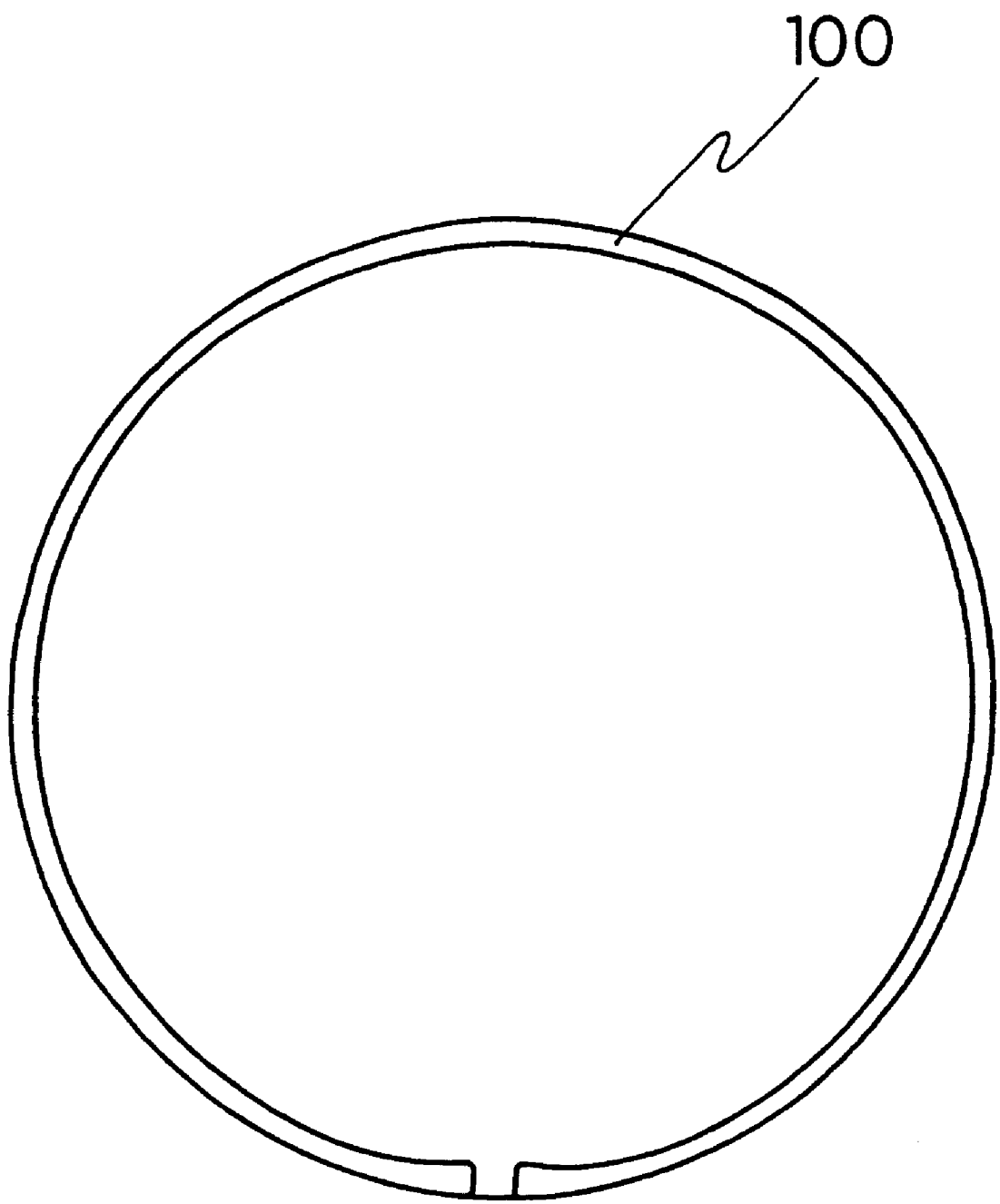
FIG. 34 is a plan view showing a state of the ring of FIG. 33, which is inserted into a capsule.
Figure 35:
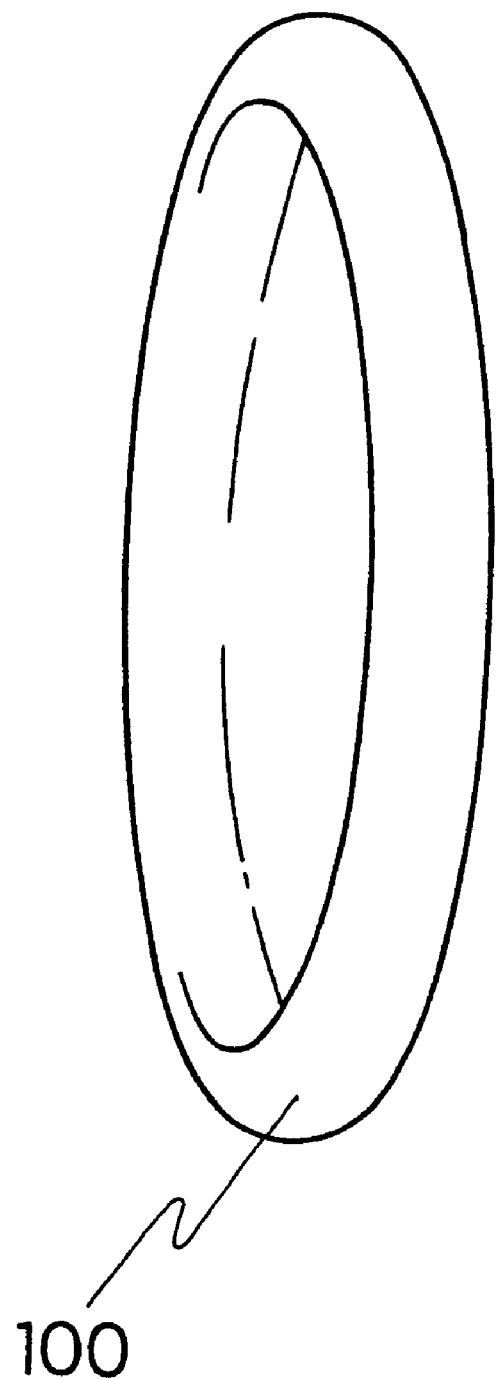
FIG. 35 is a perspective view showing still another example of the ring of FIG. 24.
Figure 36:
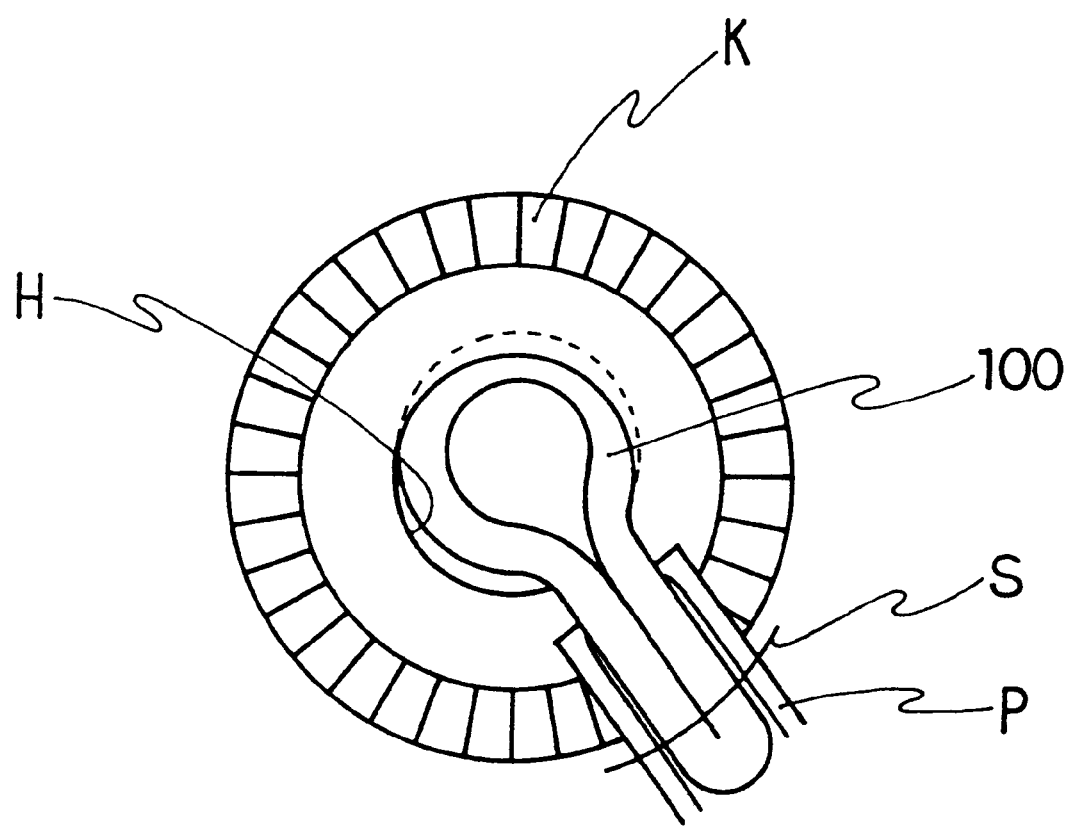
FIG. 36 is an explanatory view showing a method for inserting a conventional ring into a capsule.
Figure 37:
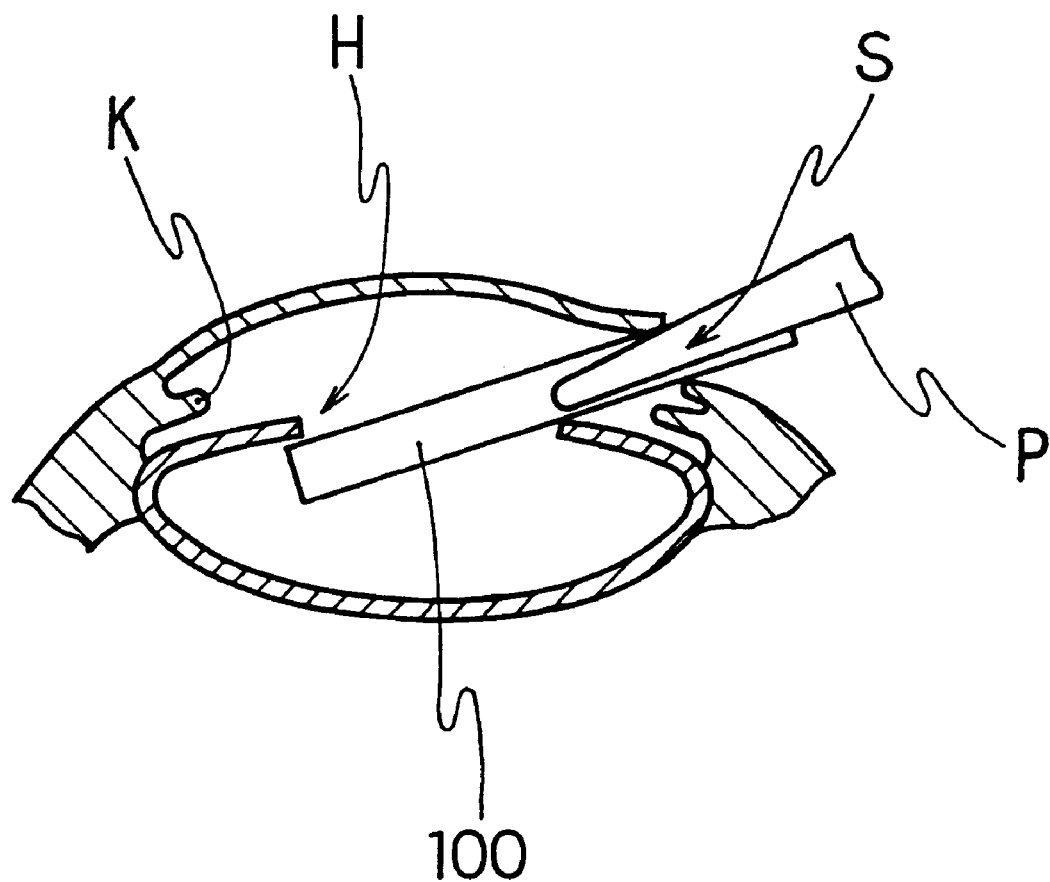
FIG. 37 is an explanatory view showing a method for inserting a conventional ring into a capsule.

As shown in FIGS. 24, 25 and 26, the ring 1 of EMBODIMENT 5 is characterized in that a flange portion FL is located in a position where both ends of the ring 1 are abutted to each other.

As the shape of the flange FL, not only the shape shown in FIGS. to 26, but also the shape shown in FIGS. 27(a) to 27(e), 28(a) to 28(d), 29(a) to 29(c) and 30(a) to 30(c) can be employed.

According to the present invention, since it is an intraocular ring of open ring shape when inserting, it can be inserted from a small incision, and after being inserted into the capsule, by engaging the engaging mechanisms having mutually complementary male and female structures provided at ends of the intraocular ring, the intraocular ring having a nearly same compressive load as in closed ring is obtained.

What is claimed is:

1. An intraocular ring for capsular shape retention made of an elastic material, in which said intraocular ring has two ends, engaging mechanisms are provided at both ends, in a partially cut-off state of the intraocular ring, and the intraocular ring has a continuous ring shape without a cut section, defining an unobstructed circular opening, when the engaging mechanisms are engaged with each other, the ring being in elastic tension in an engaged state of the engaging mechanisms such that the ring would tend to reach a discontinuous or open state.

2. The intraocular ring of claim 1, wherein the ring engaging mechanisms include mutually complementary male and female structures.

3. An intraocular ring for capsular shape retention which is partially cut-off intraocular ring made of an elastic material, in which said intraocular ring has two ends, and an intraocular ring has a continuous ring shape, defining an unobstructed circular opening, when both ends of the cut-off intraocular ring contact with each other, the ring being in elastic tension in an abutted state of the cut section of the intraocular ring such that the ring would tend to reach a discontinuous or open state.

4. The intraocular ring of claim 3, wherein both ends of the intraocular ring are formed in a taper.

5. An intraocular ring for capsular shape retention comprising two or more parts made of an elastic material, in which each of the two or more parts is in the form of a ring portion, the two or more parts individually engaging mechanisms provided at both ends so that arbitrary adjacent parts may be engaged with each other in a male-female structure, and the intraocular ring has a continuous ring shape without a cut section, defining an unobstructed circular opening, when the two or more parts are mutually engaged with each other.

6. The intraocular ring of claim 5, wherein the ring is under a compressive load in an engaged state of the cut sections of the ring.

7. The intraocular ring of claim 1 or claim 6, wherein the elastic tension corresponds to a load of about 250 mgf or more.

8. The intraocular ring of claim 3, wherein the elastic tension corresponds to a load of about 250 mgf or more.

9. The intraocular ring of claim 3, wherein at least one of both ends of the intraocular ring is provided with a flange.

* * * * *